United States Patent
Krishnan

(10) Patent No.: US 9,456,822 B2
(45) Date of Patent: Oct. 4, 2016

(54) APPARATUS AND METHOD FOR TREATING BLEEDING ARISING FROM LEFT ATRIAL APPENDAGE

(71) Applicant: Subramaniam Chitoor Krishnan, Sacramento, CA (US)

(72) Inventor: Subramaniam Chitoor Krishnan, Sacramento, CA (US)

( * ) Notice: Subject to any disclaimer, the term of this patent is extended or adjusted under 35 U.S.C. 154(b) by 0 days.

(21) Appl. No.: 14/941,457

(22) Filed: Nov. 13, 2015

(65) Prior Publication Data

US 2016/0066923 A1 Mar. 10, 2016

Related U.S. Application Data

(63) Continuation of application No. 13/922,070, filed on Jun. 19, 2013.

(60) Provisional application No. 61/661,350, filed on Jun. 19, 2012.

(51) Int. Cl.
*A61M 29/00* (2006.01)
*A61B 17/12* (2006.01)

(52) U.S. Cl.
CPC ..... *A61B 17/12122* (2013.01); *A61B 17/1204* (2013.01); *A61B 17/12045* (2013.01); *A61B 17/12136* (2013.01)

(58) Field of Classification Search
CPC . A61F 2/958; A61B 17/12; A61B 17/12122; A61B 17/12045; A61B 17/00491; A61B 17/0057; A61M 29/00; A61M 25/088; A61M 25/10
See application file for complete search history.

(56) References Cited

U.S. PATENT DOCUMENTS

| | | | |
|---|---|---|---|
| 6,423,051 B1 | 7/2002 | Kaplan et al. | |
| 6,610,072 B1 * | 8/2003 | Christy | A61B 17/0483 606/144 |
| 7,951,069 B2 | 5/2011 | Bertolero | |
| 2004/0044361 A1 | 3/2004 | Frazier et al. | |
| 2006/0027553 A1 | 2/2006 | Hanisko | |
| 2007/0129753 A1 | 6/2007 | Quinn et al. | |
| 2008/0033457 A1 * | 2/2008 | Francischelli | A61B 17/0057 606/142 |
| 2008/0183130 A1 | 7/2008 | Lutter | |
| 2009/0051270 A1 | 2/2009 | Yamazaki | |
| 2010/0191279 A1 | 7/2010 | Kassab et al. | |
| 2010/0286718 A1 | 11/2010 | Kassab | |
| 2011/0082495 A1 | 4/2011 | Ruiz | |
| 2011/0276075 A1 | 11/2011 | Fung et al. | |
| 2012/0065667 A1 | 3/2012 | Javois et al. | |

* cited by examiner

*Primary Examiner* — Victor Nguyen
(74) *Attorney, Agent, or Firm* — Snell & Wilmer LLP

(57) ABSTRACT

Bleeding arising from the left atrial appendage (LAA) can have fatal consequences because it can result in cardiac tamponade. The present invention provides apparatuses and methods for treating and preventing bleeding arising from the LAA, at the pre-hemorrhage and post-hemorrhage stages. In particular, catheters having inflatable catheter balloons are advanced into the LAA and the inflatable catheter balloons are inflated in and around the LAA in a manner that occludes the LAA ostium and the LAA cavity. Additionally, electromagnetic coils are present within the inflatable catheter balloons to create electromagnetic forces that help to further occlude the LAA ostium firmly. When the catheter balloons are inflated, these electromagnetic coils also expand. Alternatively, the LAA ostium can be occluded using electromagnetic coils present in an inflated endocardial catheter balloon and electromagnetic coils present in an inflated epicardial catheter balloon deployed around the circumference of the LAA ostium epicardially.

11 Claims, 18 Drawing Sheets

APPARATUS AND METHOD FOR TREATING BLEEDING ARISING FROM LEFT ATRIAL APPENDAGE

CROSS REFERENCE TO RELATED APPLICATIONS

This application is a continuation of prior U.S. patent application Ser. No. 13/922,070, entitled "APPARATUS AND METHOD FOR TREATING BLEEDING ARISING FROM LEFT ATRIAL APPENDAGE," filed Jun. 19, 2013, which claims the benefit and priority of U.S. Provisional Patent Application No. 61/661,350, entitled "NOVEL TECHNOLOGY FOR TREATING HEMORRHAGE FROM LEFT ATRIAL APPENDAGE," filed on Jun. 19, 2012, the entire contents and disclosures of each of these applications being hereby incorporated by reference herein.

BACKGROUND

1. Field

The present invention relates generally to apparatuses and methods for treating and preventing bleeding arising from the left atrial appendage using catheters having inflatable catheter balloons, at the pre-hemorrhage and post-hemorrhage stages.

2. Description of the Related Art

The left atrial appendage (LAA) is a small, conical, ear-shaped muscular pouch projecting from the upper anterior portion of the left atrium of the heart. Thus, the LAA lies within the pericardial cavity, and is an extension of the left atrium. The LAA functions as a decompression chamber during left ventricular systole and during periods when left atrial pressure is high. The LAA is also commonly known as the left auricular appendix, the auricular, or the left auricle. The left atrium receives oxygenated blood from the lungs by way of the pulmonary veins, and pumps the oxygenated blood into the left ventricle via the mitral valve.

Over the past 8 to 10 years, the LAA has become the target of several invasive procedures due to the high likelihood of embolic strokes arising from the LAA. During these procedures, bleeding arising from the LAA can occur. Additionally during these procedures, there can be tearing of the LAA. It is also anticipated that in the next few years, the number of invasive procedures involving the LAA is going to rise significantly. Invasive procedures of the heart targeting or involving the LAA is especially expected in patients who have atrial fibrillation (AF) and who may be at an increased risk of stroke arising from the LAA.

Bleeding arising from the LAA into the pericardial cavity is an emergent situation that requires immediate attention to stabilize the patient. If the bleeding is severe, cardiac tamponade can result and there may not be sufficient time to transfer the patient to an operating room for the proper care. Additionally, elderly patients are often not candidates for cardiac surgery due to advanced age and other comorbid issues. Thus, there is a need for novel percutaneous technologies and procedural techniques to treat hemorrhage arising from the LAA without subjecting the patient to cardiac surgery.

Additionally, there may also be a need to prevent bleeding arising from the LAA at the pre-hemorrhage stage, i.e. prior to the actual bleeding especially if the patient is to undergo a procedure involving the LAA, particularly where, as part of the procedure, the LAA may be intentionally pierced or perforated. The novel technology presented in this invention allows a puncture from the LAA onto the pericardial space or vice versa in a controlled setting without the development of hemorrhage into the pericardial cavity.

AF causes rapid randomized contractions of the atrial myocardium, resulting in an irregular and rapid ventricular rate and is currently, the most common type of cardiac arrhythmia. It affects more than 3 million patients in the United States, and this number is expected to climb to 16 million by 2050. AF is the most common cause of strokes arising from the heart due a blood clot forming in the heart.

Embolic stroke interrupts blood flow to the brain, thereby causing the affected brain cells to die. When brain cells die, the abilities controlled by the dying brain cells are compromised and eventually lost. In the United States, stroke is the third leading cause of death, killing approximately 160,000 Americans each year. Additionally, stroke is the leading cause of adult disability and there are currently over four million Americans living with the effects of stroke.

AF patients have a five-fold increased risk of an embolic stroke resulting primarily from thromboembolic events. In non-rheumatic AF patients, the stroke-causing thrombus originates almost exclusively from the LAA. Typically, the thrombus formed in the LAA break away from the LAA and accumulates in other blood vessels, thereby blocking blood flow in these blood vessels, and ultimately leading to an embolic stroke. Thus, the occlusion, stapling or ligation of the LAA is believed to be an effective stroke prevention technique. Several existing medical procedures aim to prevent the migration of thrombus from the LAA.

Commonly, rheumatic and non-rheumatic AF patients are administered warfarin, which is a therapeutic drug classified as an anticoagulant that helps prevent thromboembolism. An anticoagulant drug is a drug that suppresses, delays, or nullifies blood coagulation. Warfarin has the chemical name, 4-hydroxy-3-oxo-1-phenylbutyl-2H-benzopyran-2-one, and molecular formula, $C_{19}H_{16}O_4$. However, a major drawback of warfarin is the difficulty of maintaining its therapeutic range, and thus, warfarin-administered patients require frequent monitoring and dose adjustments.

Alternatively, in patients intolerant of warfarin, occlusion of the LAA is believed to decrease the risk of an embolic stroke in non-valvular AF patients. Occlusion of the LAA is an obstruction or a closure of the LAA. By occluding the LAA, the thrombus formed in the LAA are unable to migrate to other blood vessels, thereby reducing the risks of thromboembolism and embolic stroke. Hence, the occlusion of the LAA is believed to be an effective stroke prevention strategy in non-valvular AF patients. Indeed, this concept of occluding the LAA as a stroke prevention strategy is being increasingly tested with implantable medical devices that occlude the LAA.

For example, the WATCHMAN device developed by Atritech Inc. (Plymouth, Minn.) is an implantable medical device designed to occlude the LAA in non-valvular AF patients. In particular, the WATCHMAN device is placed distal to the ostium of the LAA, thereby occluding the LAA. The occlusion of the LAA prevents the migration of the thrombus formed in the LAA, thereby reducing the risks of thromboembolism and embolic stroke. In the WATCHMAN device's clinical trial, PROTECT-AF trial, the results showed that in AF patients who were candidates for warfarin therapy, the closure of the LAA using the WATCHMAN device was associated with a reduction in hemorrhagic stroke risk as compared to warfarin therapy. Additionally, these results showed that all-cause stroke and all-cause mortality outcomes were non-inferior to warfarin.

However, a major drawback of the WATCHMAN device is the fixation of barbs or wires engaged in the walls of the LAA, thereby causing adverse events. As shown in the PROTECT-AF trial, a major adverse event is pericardial effusion, which is the abnormal accumulation of fluid in the pericardial cavity, which can negatively affect heart function. Another adverse event is the tearing of the walls of the LAA by the barb wires, thereby necessitating emergent surgery. The tearing of the LAA may lead to bleeding, which is an emergent situation that requires quick, decisive action to stop the bleeding and stabilize the patient.

Ligation of the LAA is yet another stroke prevention technique for patients intolerant of warfarin. In particular, the LAA is ligated with a suture using a percutaneous epicardial approach, resulting in a complete closure of the LAA. However, like the WATCHMAN device, a major drawback of this approach is the risks of bleeding and tears in the LAA.

Tears and bleeding arising from the LAA is particularly concerning for elderly patients because due to their advanced age, the walls of their LAA are fragile. As a result, elderly patients are more susceptible to tears and bleeding. Additionally, elderly patients are not candidates for cardiac surgery due to their advanced age and other significant comorbid issues.

In light of the foregoing, there is a compelling need for novel technologies and procedural techniques for treating and preventing bleeding arising from the LAA, at the pre-hemorrhage and post-hemorrhage stages, without subjecting the patient to cardiac surgery.

SUMMARY OF THE INVENTION

The present invention addresses the foregoing needs with apparatuses and methods for treating and preventing bleeding arising from the LAA, at the pre-hemorrhage and post-hemorrhage stages, using catheters comprising of inflatable catheter balloons.

In an exemplary embodiment, a method for treating and preventing bleeding arising from the LAA comprises the steps of introducing a catheter into a body cavity, advancing a guide wire tip and a catheter sheath of the catheter to and through an ostium of the LAA, and into a cavity of the LAA, inflating a first inflatable catheter balloon having a first set of electromagnetic coils, wherein upon inflation of the first catheter balloon, the first set of electromagnetic coils also expand, performing a tug test on the inflated first catheter balloon to occlude the LAA ostium, inflating a second inflatable catheter balloon, and inflating a third inflatable catheter balloon having a second set of electromagnetic coils, and wherein upon inflation of the third catheter balloon, the second set of electromagnetic coils also expand. Alternatively, the third inflatable catheter balloon can be inflated before the second inflatable catheter balloon. The method further comprising the step of puncturing the LAA cavity, wherein the puncturing is in a direction from within the LAA cavity and into a pericardial cavity. The method, wherein the body cavity is a femoral vein, a jugular vein, an axillary vein, a subclavian vein, or an apex of a left ventricle.

In another exemplary embodiment, a method for treating and preventing bleeding arising from the LAA comprises the steps of introducing a catheter into a body cavity, advancing a guide wire tip and an inner catheter sheath of the catheter to and through an ostium of the LAA, and into a cavity of the LAA, inflating a first inflatable catheter balloon, pulling the inflated first catheter balloon, from the LAA cavity and towards the LAA ostium, to occlude the LAA ostium, advancing an outer catheter sheath of the catheter towards the guide wire tip, inflating a second inflatable catheter balloon, and pushing the inflated second catheter balloon, from the left atrium and towards the LAA ostium, to occlude the LAA ostium. The method further comprises the step of deploying means for locking in place the inflated first catheter balloon and the inflated second catheter balloon. The method further comprising the step of puncturing the LAA cavity, wherein the puncturing is in a direction from within the LAA cavity and into a pericardial cavity. The method, wherein the body cavity is a femoral vein, a jugular vein, an axillary vein, a subclavian vein, or an apex of a left ventricle.

In another exemplary embodiment, a method for treating and preventing bleeding arising from the LAA comprises the steps of introducing a catheter into a cavity of the LAA, advancing a guide wire tip of the catheter to and through an ostium of the LAA, and into a left atrium, advancing a catheter sheath of the catheter towards the guide wire tip, inflating a first inflatable catheter balloon having a first set of electromagnetic coils, and wherein upon inflation of the first catheter balloon, the first set of electromagnetic coils also expand, pulling the inflated first catheter balloon from the left atrium and towards the LAA ostium, and inflating a second inflatable catheter balloon having a second set of electromagnetic coils.

In another exemplary embodiment, a method for treating and preventing bleeding arising from the LAA comprises the steps of introducing a catheter into a cavity of the LAA, advancing a guide wire tip of the catheter to and through an ostium of the LAA, and into a left atrium, advancing a catheter sheath of the catheter towards the guide wire tip, inflating a first inflatable endocardial catheter balloon having a first set of electromagnetic coils, and wherein upon inflation of the first endocardial catheter balloon, the first set of electromagnetic coils also expand, pulling the inflated first endocardial catheter balloon from the left atrium and towards the LAA ostium, deploying a constricting circumferential inflatable epicardial catheter balloon, having a second set of electromagnetic coils, around a circumference of the LAA ostium epicardially, inflating the epicardial catheter balloon, wherein upon inflation of the epicardial catheter balloon, the second set of electromagnetic coils also expand, and inflating a second inflatable endocardial catheter balloon affixed to the catheter sheath. Alternatively, the second inflatable endocardial catheter balloon comprises a third set of electromagnetic coils, wherein upon inflation of the second endocardial catheter balloon, the third set of electromagnetic coils also expand.

The contents of this summary section are provided only as a simplified introduction to the invention, and are not intended to be used to limit the scope of the appended claims.

BRIEF DESCRIPTION OF THE DRAWINGS

Other systems, methods, features and advantages of the present invention will be or will become apparent to one of ordinary skill in the art upon examination of the following figures and detailed description. It is intended that all such additional apparatuses, systems, methods, features and advantages be included within this description, be within the scope of the present invention, and be protected by the appended claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Figure 1:
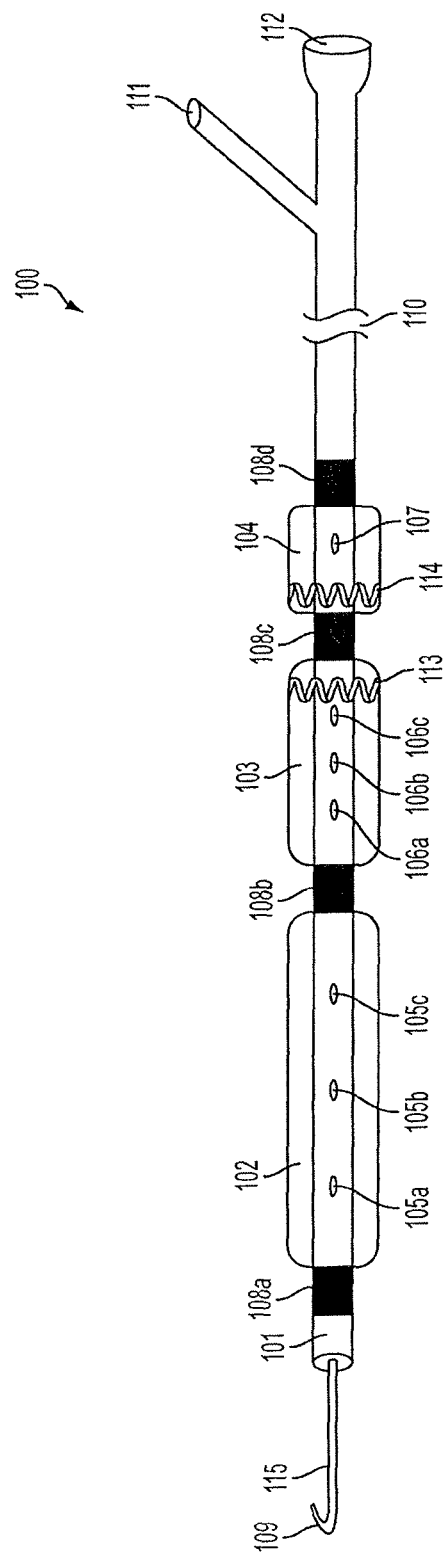
FIG. 1 is a perspective view of an exemplary embodiment of the present invention's apparatus for treating and preventing bleeding arising from the LAA.
Figure 8:
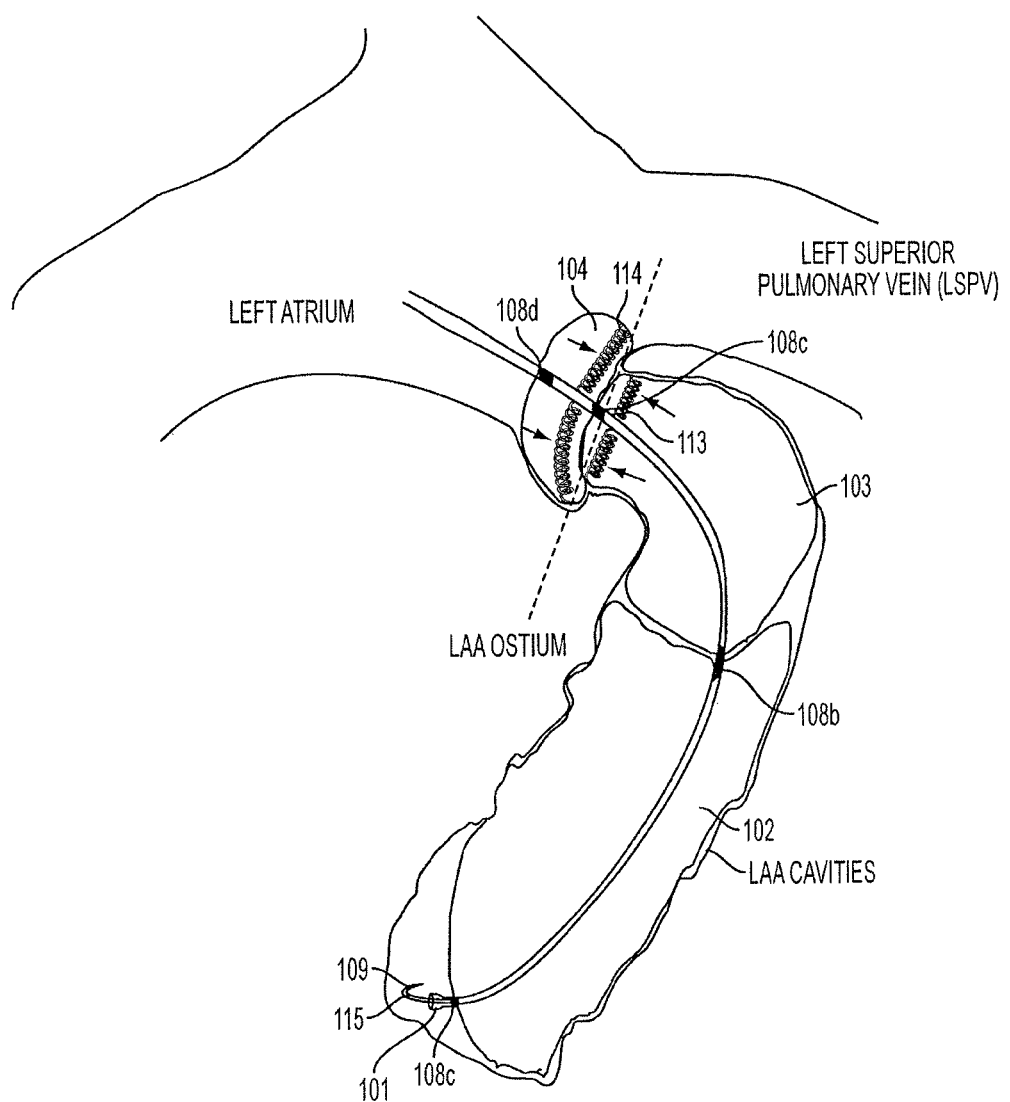
FIG. 8 is a third perspective view of the exemplary embodiment of FIG. 1 when deployed into the LAA.

FIG. 1 is a perspective view of an exemplary embodiment of the present invention's apparatus for treating and preventing bleeding arising from the LAA. FIG. 1 shows a stand-alone catheter 100 before it is introduced into a body cavity. Hence, FIG. 1 shows inflatable catheter balloons 102, 103, and 104 in their un-inflated form. Inflatable catheter balloons 102, 103, and 104 are affixed to catheter sheath 101. Depending on the desired degree of compliance, inflatable catheter balloons 102, 103, and 104 can be made of rubber, latex, polyisoprene, silicone, polyurethane, or any combination thereof. Rubber, latex, polyisoprene, and silicone produce more compliant inflatable catheter balloons. Polyurethane produces less compliant inflatable catheter balloons. A mixture of silicone and polyurethane produces half-way compliant inflatable catheter balloons. In this exemplary embodiment of FIG. 1, inflatable catheter balloon 102 is more compliant because when inflated, its shape assumes the contours of its surroundings in the LAA cavity, as shown in FIG. 8. On the other hand, a semi-compliant or a non-compliant inflatable catheter balloon will likely deform and expand the wall of the LAA. It is contemplated that inflatable catheter balloons 102, 103, and 104 can be compliant, semi-compliant, or non-compliant, or any combination of the foregoing. Additionally, it is contemplated that catheter 100 can be made up of only one inflatable catheter balloon, two inflatable catheter balloons, or more than three inflatable catheter balloons.

Inflatable catheter balloon 102 is inflated with the input of air, or a liquid material that is mixed with radiopaque contrast, via inflation port 111 through catheter sheath openings 105a, 105b, and 105c. Inflatable catheter balloon 103 is inflated with the input of air, or a liquid material that is mixed with radiopaque contrast, via inflation port 111 through catheter sheath openings 106a, 106b, and 106c. Inflatable catheter balloon 104 is inflated with the input of air, or a liquid material that is mixed with radiopaque contrast, via inflation port 111 through catheter sheath opening 107. It is contemplated that the number of catheter sheath openings can vary. For example, inflatable catheter balloon 102 can be inflated via inflation port 111 through only one catheter sheath opening, or through more than three catheter sheath openings. Inflation port 111 provides the portal for the input of air, or a liquid material that is mixed with radiopaque contrast, by, for example, a balloon catheter inflation device.

When inflated, inflatable catheter balloon 102 has a larger area than that of inflatable catheter balloon 103, as shown in FIG. 8. When inflated, inflatable catheter balloon 103 has a larger area than inflatable catheter balloon 104, as shown in FIG. 8. When inflated, inflatable catheter balloon 104 has a larger diameter than that of the LAA ostium, and those of inflatable catheter balloons 102 and 103, as shown in FIG. 8. Thus, when inflated, inflatable catheter balloon 104 has a larger circumference than that of the LAA ostium, and those of inflatable catheter balloons 102 and 103, as shown in FIG. 8.

Electromagnetic coils 113 are located within the proximal portions of inflatable catheter balloon 103. Electromagnetic coils 114 are located within the distal portions of inflatable catheter balloon 104. When inflatable catheter balloons 103 and 104 are inflated, electromagnetic coils 113 and 114 also expand, as shown in FIG. 8. Electromagnetic coils 113 and 114 are insulated wires coiled together to form a solenoid, and thus, can be made out of copper or any other metallic wire capable of conducting electricity.

Guide wire tip 109 is a J-hooked, soft-tipped guide wire. Guide wire tip 109 is the first component of catheter 100 introduced into the body cavity. Guide wire tip 109 guides catheter 100 to the desired location.

As duly noted by elongation identifier 110, the length of guide wire 115 can vary depending on where guide wire tip 109 is introduced into the body cavity, and the body cavity dimensions of the particular patient. Similarly, as duly noted by elongation identifier 110, the length of catheter sheath 101 can vary depending on where guide wire tip 109 is introduced into the body cavity, and the body cavity dimensions of the particular patient.

Radiopaque marker bands 108a, 108b, 108c, and 108d are thin metal tubes affixed along catheter sheath 101 to provide spatial guidance under an X-ray fluoroscope. Radiopaque marker band 108a marks the distal end of inflatable catheter balloon 102. Radiopaque marker band 108b marks the intersection of the proximal end of inflatable catheter balloon 102 and the distal end of inflatable catheter balloon 103. Radiopaque marker band 108c marks the intersection of the proximal end of inflatable catheter balloon 103 and the distal end of inflatable catheter balloon 104, and when catheter 100 is introduced into the body cavity, radiopaque marker band 108c marks the mid-point of the LAA ostium, as shown in FIG. 8. Radiopaque marker band 108d marks the distal end of inflatable catheter balloon 104.

Control port 112 provides the portal for connection to catheter handling devices designed to control and navigate guide wire tip 109 and guide wire 115 to the desired location. Control port 112 also provides the portal for the insertion of additional guide wire for guide wire 115.

Figure 2:
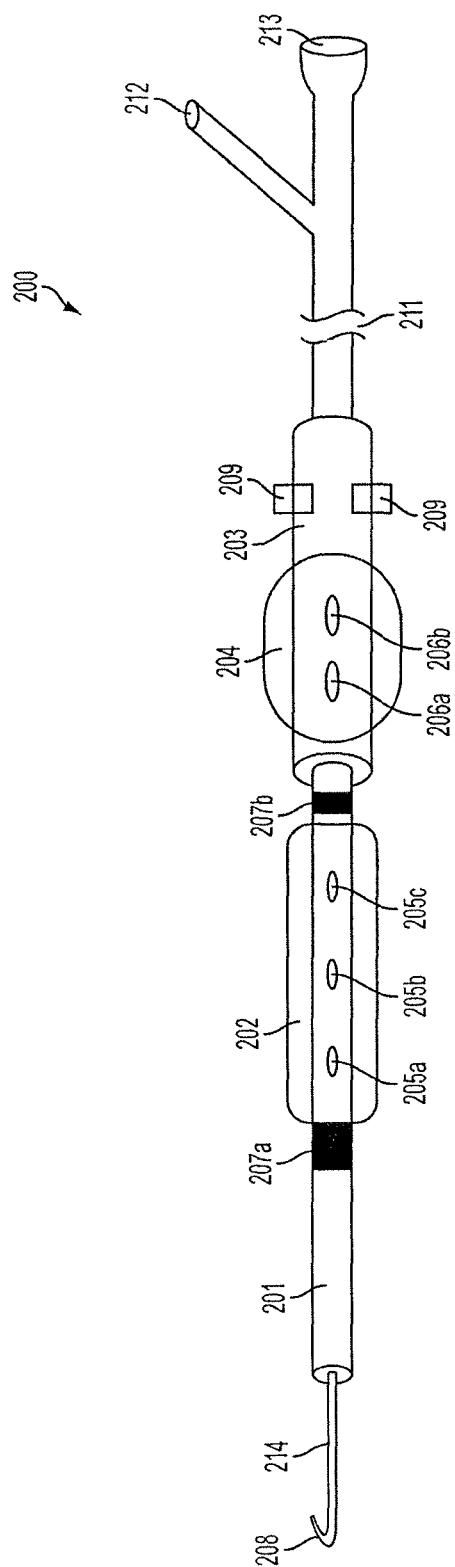
FIG. 2 is a perspective view of a second exemplary embodiment of the present invention's apparatus for treating and preventing bleeding arising from the LAA.
Figure 16:
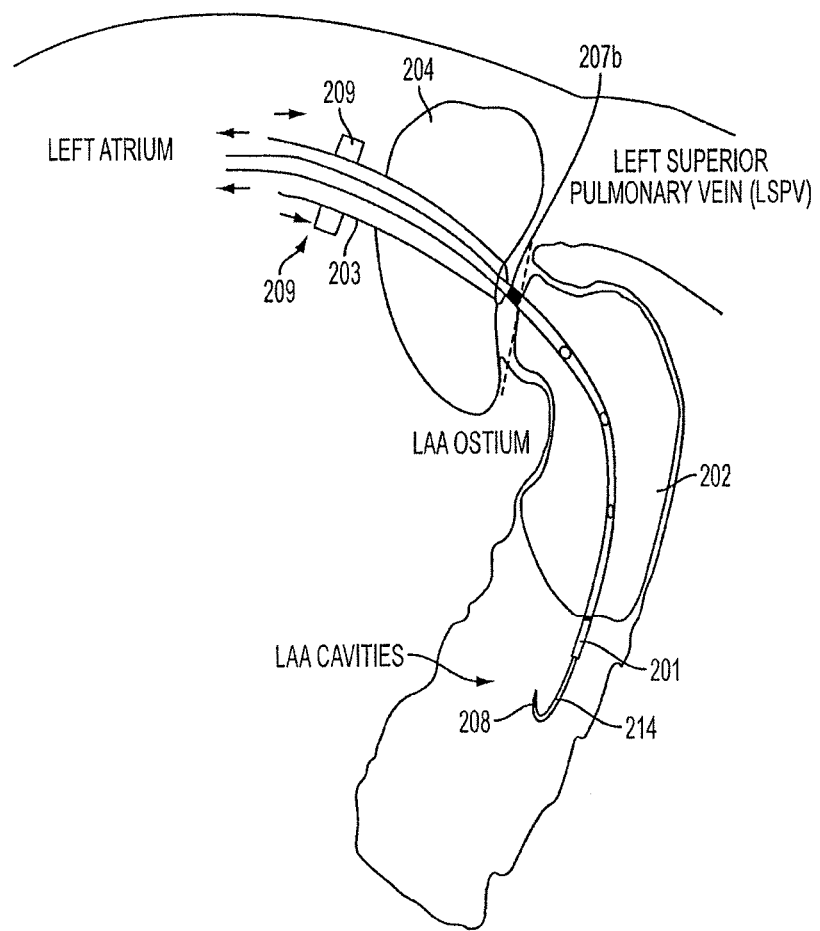
FIG. 16 is a perspective view of the exemplary embodiment of FIG. 2 when deployed into the LAA.

FIG. 2 is a perspective view of a second exemplary embodiment of the present invention's apparatus for treating and preventing bleeding arising from the LAA. FIG. 2 shows a stand-alone catheter 200 before it is introduced into a body cavity. Hence, FIG. 2 shows inflatable catheter balloons 202 and 204 in their un-inflated form. Inflatable catheter balloon 202 is affixed to inner catheter sheath 201. Inflatable catheter balloon 204 is affixed to outer catheter sheath 203. As previously articulated, depending on the desired degree of compliance, inflatable catheter balloons 202 and 204 can be made of rubber, latex, polyisoprene, silicone, polyurethane, or any combination thereof. In this exemplary embodiment of FIG. 2, inflatable catheter balloon 202 is more compliant because when inflated, its shape assumes the contours of its surroundings in the LAA cavity, as shown in FIG. 16. On the other hand, a semi-compliant or a non-compliant inflatable catheter balloon will likely deform and expand the wall of the LAA. It is contemplated that inflatable catheter balloons 202 and 204 can be compliant, semi-compliant, or non-compliant, or any combination of the foregoing. Additionally, it is contemplated that catheter 200 can be made up of only one inflatable catheter balloon, or more than two inflatable catheter balloons. For example, an additional inflatable catheter balloon, distal to inflatable catheter balloon 202 and radiopaque marker band 207a on inner catheter sheath 201, can be affixed to inner catheter sheath 201.

Inflatable catheter balloon 202 is inflated with the input of air, or a liquid material that is mixed with radiopaque contrast, via inflation port 212 through catheter sheath openings 205a, 205b, and 205c. Similarly, inflatable catheter balloon 204 is inflated with the input of air, or a liquid material that is mixed with radiopaque contrast, via inflation port 212 through catheter sheath openings 206a and 206b. It is contemplated that the number of catheter sheath openings can vary. For example, inflatable catheter balloon 202 can be inflated via inflation port 212 through only one catheter sheath opening, or through more than three catheter sheath openings. Inflation port 212 provides the portal for the input of air by, or a liquid material that is mixed with radiopaque contrast, by, for example, a balloon catheter inflation device.

When inflated, inflatable catheter balloon 204 has a larger diameter than that of the LAA ostium, and that of inflatable catheter balloon 202, as shown in FIG. 16. Thus, when inflated, inflatable catheter balloon 204 has a larger circumference than that of the LAA ostium, and that of inflatable catheter balloon 202, as shown in FIG. 16.

Guide wire tip 208 is a J-hooked, soft-tipped guide wire. Guide wire tip 208 is the first component of catheter 200 introduced into the body cavity. Guide wire tip 208 guides catheter 200 to the desired location.

As duly noted by elongation identifier 211, the length of guide wire 214 can vary depending on where guide wire tip 208 is introduced into the body cavity, and the body cavity dimensions of the particular patient. Similarly, as duly noted by elongation identifier 211, the length of inner catheter sheath 201 and outer catheter sheath 203 can vary depending on where guide wire tip 208 is introduced into the body, and the body cavity dimensions of the particular patient.

Radiopaque marker bands 207a and 207b are thin metal tubes placed along inner catheter sheath 201 to provide spatial guidance under an X-ray fluoroscope. Radiopaque marker band 207a marks the distal end of inflatable catheter balloon 202. Radiopaque marker band 207b marks the intersection of the proximal end of inflatable catheter balloon 202 and the distal end of inflatable catheter balloon 204, and when catheter 200 is introduced into the body cavity, radiopaque marker band 207b marks the mid-point of the LAA ostium, as shown in FIG. 16.

Figure 17:
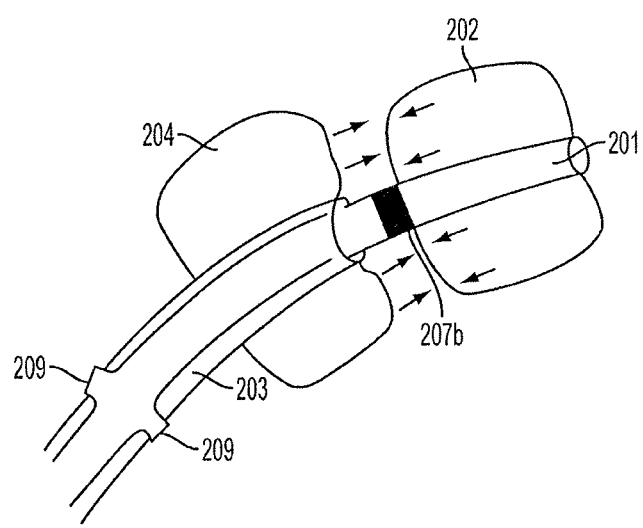
FIG. 17 is a perspective view of the locking means in the exemplary embodiment of FIG. 2.

After inflatable catheter balloons 202 and 204 are inflated, locking means 209 is deployed, as shown in FIGS. 16 and 17. Locking means 209 is shown in FIG. 17. Locking means 209 is a spring-loaded device housed in inner catheter sheath 202 that upon deployment, it would bulge out through the corresponding slots in outer catheter sheath 203, thereby locking in place inflatable catheter balloons 202 and 204.

Control port 213 provides the portal for connection to catheter handling devices designed to control and navigate guide wire tip 208 and guide wire 214 to the desired location. Control port 213 also provides the portal for the insertion of additional guide wire for guide wire 214.

Figure 3:
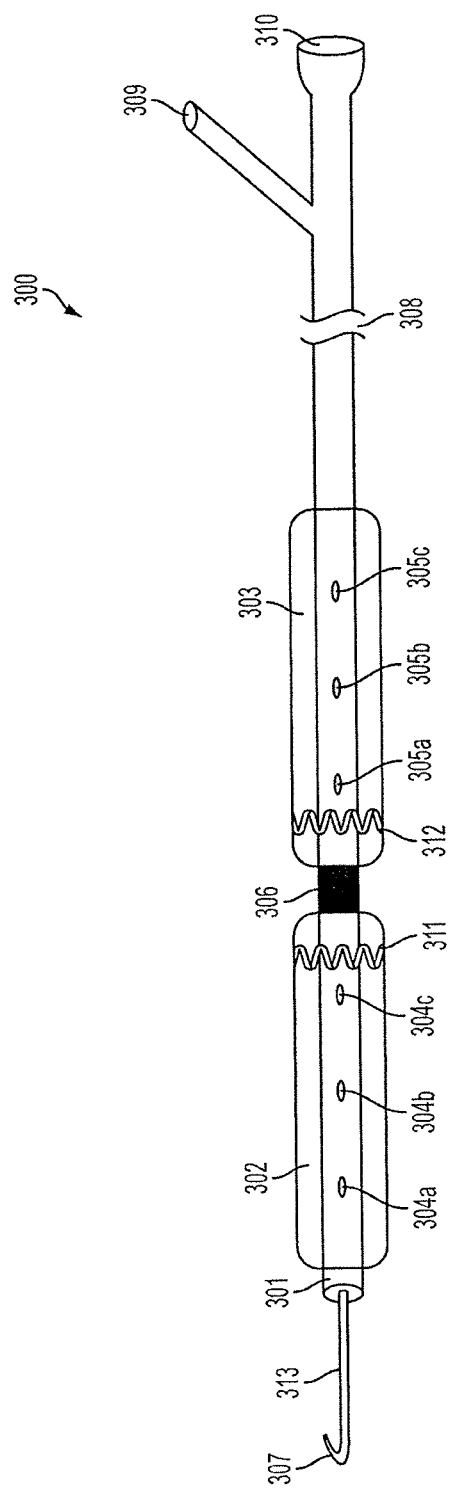
FIG. 3 is a perspective view of a third exemplary embodiment of the present invention's apparatus for treating and preventing bleeding arising from the LAA.
Figure 12:
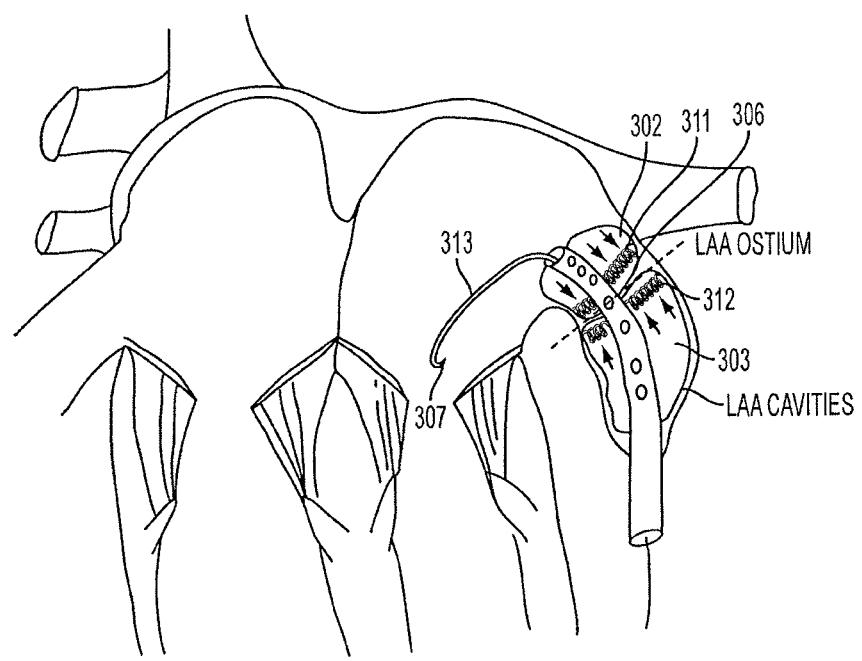
FIG. 12 is a third perspective view of the exemplary embodiment of FIG. 3 when deployed into the LAA.

FIG. 3 is a perspective view of a third exemplary embodiment of the present invention's apparatus for treating and preventing bleeding arising from the LAA. FIG. 3 shows a stand-alone catheter 300 before it is introduced into a body cavity. Hence, FIG. 3 shows inflatable catheter balloons 302 and 303 in their un-inflated form. Inflatable catheter balloons 302 and 303 are affixed to catheter sheath 301. As previously articulated, depending on the desired degree of compliance, inflatable catheter balloons 302 and 303 can be made of rubber, latex, polyisoprene, silicone, polyurethane, or any combination thereof. In this exemplary embodiment of FIG. 3, inflatable catheter balloon 303 is more compliant because when inflated, its shape assumes the contours of its surroundings in the LAA cavity, as shown in FIG. 12. On the other hand, a semi-compliant or a non-compliant catheter balloon will likely deform and expand the wall of the LAA. It is contemplated that inflatable catheter balloons 302 and 303 can be compliant, semi-compliant, or non-compliant, or any combination of the foregoing. Additionally, it is contemplated that catheter 300 can be made up of only one inflatable catheter balloon, or more than two inflatable catheter balloons. For example, an additional inflatable catheter balloon, distal to inflatable catheter balloon 303 on catheter sheath 301, can be affixed to catheter sheath 301.

Inflatable catheter balloon 302 is inflated with the input of air, or a liquid that is mixed with radiopaque contrast, via inflation port 309 through catheter sheath openings 304a, 304b, and 304c. Similarly, inflatable catheter balloon 303 is inflated with the input of air, or a liquid that is mixed with radiopaque contrast, from inflation port 309 via catheter sheath openings 305a, 305b, and 305c. It is contemplated that the number of catheter sheath openings can vary. For example, inflatable catheter balloon 302 can be inflated via inflation port 309 through only one catheter sheath opening, or through more than three catheter sheath openings. Inflation port 309 provides the portal for the input of air, or a liquid that is mixed with radiopaque contrast, by, for example, a balloon catheter inflation device.

Electromagnetic coils 311 are located within the proximal portions of inflatable catheter balloon 302. Electromagnetic coils 312 are located within the distal portions of inflatable catheter balloon 303. When inflatable catheter balloons 302 and 303 are inflated, electromagnetic coils 311 and 312 also expand, as shown in FIG. 12. Electromagnetic coils 311 and 312 are insulated wires coiled together to form a solenoid, and thus, can be made out of copper or any other metallic wire capable of conducting electricity.

Guide wire tip 307 is a J-hooked, soft-tipped guide wire. Guide wire tip 307 is the first component of catheter 300 introduced into the body cavity. Guide wire tip 307 guides catheter 300 to the desired location.

As duly noted by elongation identifier 308, the length of guide wire 313 can vary depending on where guide wire tip 307 is introduced into the body cavity, and the body cavity dimensions of the particular patient. Similarly, as duly noted by elongation identifier 308, the length of catheter sheath 301 can vary depending on where guide wire tip 307 is introduced into the body cavity, and the body cavity dimensions of the particular patient.

Radiopaque marker band 306 is a thin metal tube placed along catheter sheath 301 to provide spatial guidance under an X-ray fluoroscope. Radiopaque marker band 306 marks the intersection of the proximal end of inflatable catheter balloon 302 and the distal end of inflatable catheter balloon 303.

Control port 310 provides the portal for connection to catheter handling devices designed to control and navigate guide wire tip 307 and guide wire 313 to the desired location. Control port 310 also provides the portal for the insertion of additional guide wire for guide wire 313.

Figure 4:
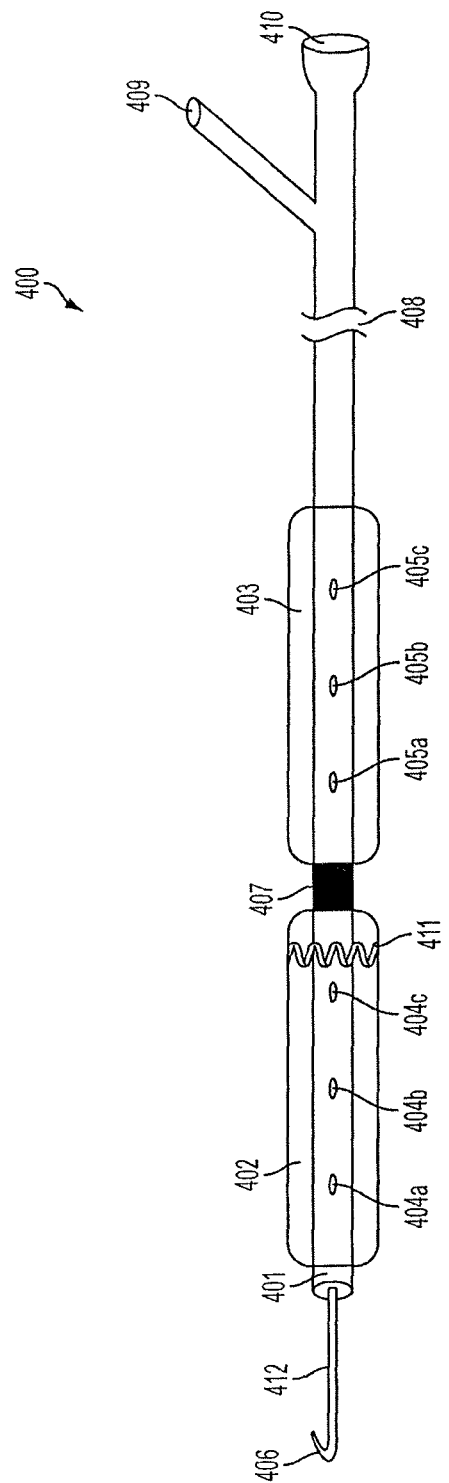
FIG. 4 is a perspective view of a fourth exemplary embodiment of the present invention's apparatus for treating and preventing bleeding arising from the LAA.
Figure 14:
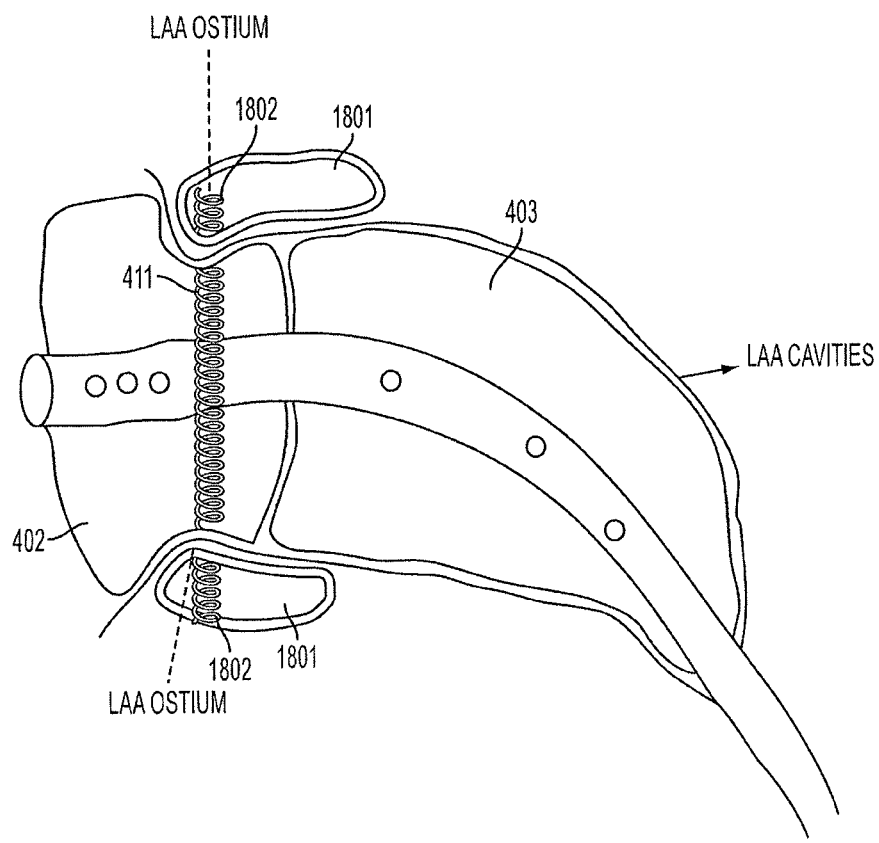
FIG. 14 is a perspective view of the exemplary embodiments of FIGS. 4 and 18A-18B when apparatus 400 is deployed into the LAA in the endocardial layer, and when apparatus 1800 is deployed around the LAA in the epicardial layer.

FIG. 4 is a perspective view of a fourth exemplary embodiment of the present invention's apparatus for treating and preventing bleeding arising from the LAA. FIG. 4 shows a stand-alone catheter 400 before it is introduced into a body cavity. Hence, FIG. 4 shows inflatable endocardial catheter balloons 402 and 403 in their un-inflated form. Inflatable endocardial catheter balloons 402 and 403 are affixed to catheter sheath 401. Depending on the desired degree of compliance, inflatable endocardial catheter balloons 402 and 403 can be made of rubber, latex, polyisoprene, silicone, polyurethane, or any combination thereof. Rubber, latex, polyisoprene, and silicone produce more compliant inflatable catheter balloons. Polyurethane produces less compliant inflatable catheter balloons. A mixture of silicone and polyurethane produces half-way compliant inflatable catheter balloons. In this exemplary embodiment of FIG. 4, inflatable endocardial catheter balloon 403 is more compliant because when inflated, its shape assumes the contours of its surroundings in the LAA cavity, as shown in FIG. 14. On the other hand, a semi-compliant or a non-compliant catheter balloon will likely deform and expand the wall of the LAA. It is contemplated that inflatable endocardial catheter balloons 402 and 403 can be compliant, semi-compliant, or non-compliant, or any combination of the foregoing. Additionally, it is contemplated that catheter 400 can be made up of more than two inflatable endocardial catheter balloons. For example, an additional inflatable endocardial catheter balloon, distal to inflatable endocardial catheter balloon 403 on catheter sheath 401, can be affixed to catheter sheath 401.

Inflatable endocardial catheter balloon 402 is inflated with the input of air, or a liquid that is mixed with radiopaque contrast, via inflation port 409 through catheter sheath openings 404a, 404b, and 404c. Similarly, inflatable endocardial catheter balloon 403 is inflated with the input of air, or a liquid that is mixed with radiopaque contrast, via inflation port 409 through catheter sheath openings 405a, 405b, and 405c. It is contemplated that the number of catheter sheath openings can vary. For example, inflatable endocardial catheter balloon 402 can be inflated via inflation port 409 through only one catheter sheath opening, or through more than three catheter sheath openings. Inflation port 409 provides the portal for the input of air, or a liquid that is mixed with radiopaque contrast, by, for example, a balloon catheter inflation device.

When inflated, the distal portions of inflatable endocardial catheter balloon 402 has a larger diameter than that of the LAA ostium, and that of inflatable endocardial catheter balloon 403, as shown in FIG. 14. Thus, when inflated, the distal portions of inflatable endocardial catheter balloon 402 has a larger circumference than that of the LAA ostium, and that of inflatable endocardial catheter balloon 403, as shown in FIG. 14.

Figure 11:
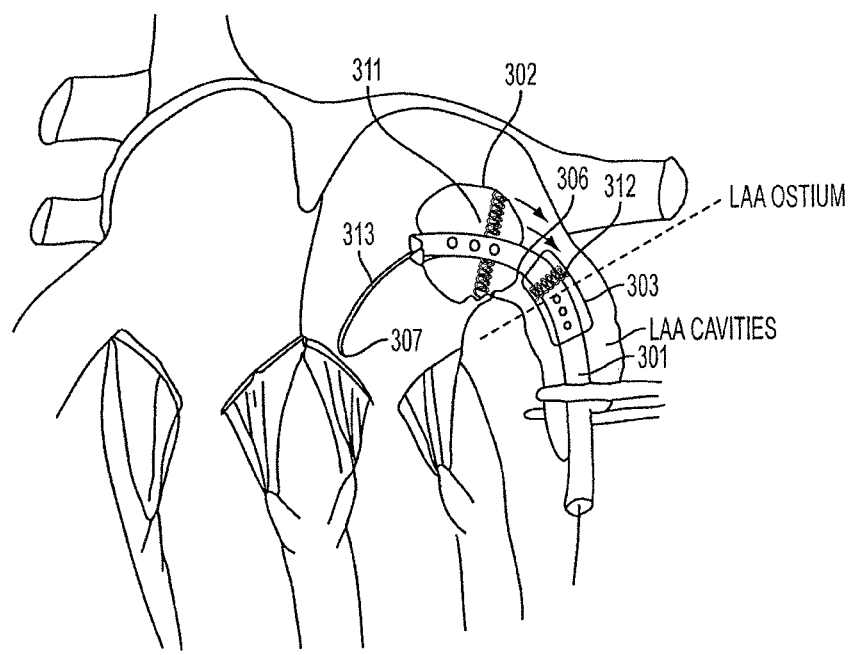
FIG. 11 is a second perspective view of the exemplary embodiment of FIG. 3 when deployed into the LAA.

Electromagnetic coils 411 are located within the proximal portions of inflatable endocardial catheter balloon 402. When inflatable endocardial catheter balloon 402 is inflated, electromagnetic coils 411 also expand, as shown in FIG. 11. Electromagnetic coils 411 are insulated wires coiled together to form a solenoid, and thus, can be made out of copper or any other metallic wire capable of conducting electricity.

Guide wire tip 406 is a J-hooked, soft-tipped guide wire. Guide wire tip 406 is the first component of catheter 400 introduced into the body cavity. Guide wire tip 406 guides catheter 400 to the desired location.

As duly noted by elongation identifier 408, the length of guide wire 412 can vary depending on where guide wire tip 406 is introduced into the body cavity, and the body cavity dimensions of the particular patient. Similarly, as duly noted by elongation identifier 408, the length of catheter sheath 401 can vary depending on where guide wire tip 406 is introduced into the body, and the body cavity dimensions of the particular patient.

Radiopaque marker band 407 is a thin metal tube placed along catheter sheath 401 to provide spatial guidance under an X-ray fluoroscope. Radiopaque marker band 407 marks the intersection of the proximal end of inflatable endocardial catheter balloon 402 and the distal end of inflatable endocardial catheter balloon 403, as shown in FIG. 14.

Control port 410 provides the portal for connection to catheter handling devices designed to control and navigate guide wire tip 406 and guide wire 412 to the desired location. Control port 410 also provides the portal for the insertion of additional guide wire for guide wire 412.

Figure 5:
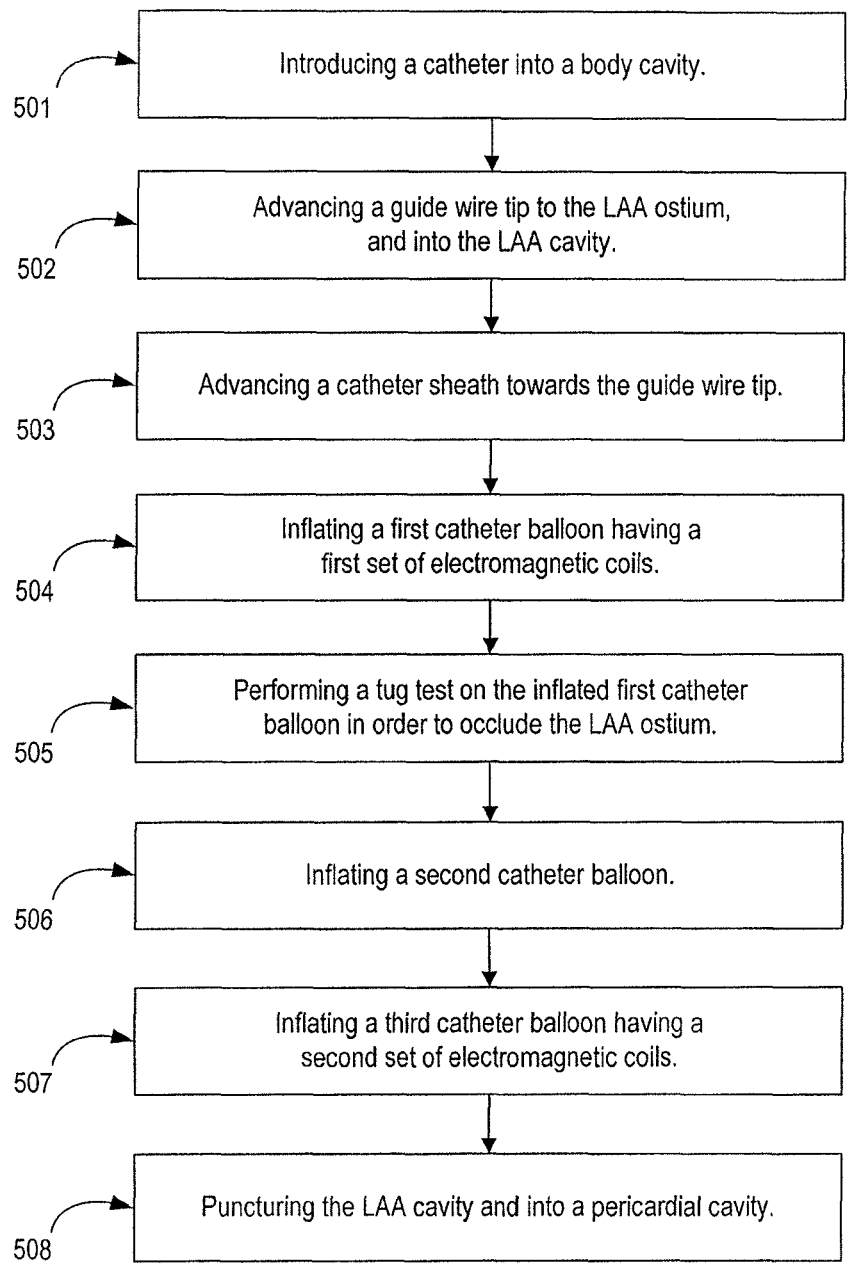
FIG. 5 is a flowchart depicting an exemplary embodiment of the present invention's method for treating and preventing bleeding arising from the LAA utilizing catheter 100 as shown in FIGS. 1, and 6-8.

FIG. 5 is a flowchart depicting an exemplary embodiment of the present invention's method for treating and preventing bleeding arising from the LAA utilizing catheter 100 as shown in FIGS. 1, and 6-8. At step 501, catheter 100 is introduced into a body cavity. For example, catheter 100 can be introduced into a body cavity via a puncture and an insertion of guide wire tip 109 into the body. Catheter 100 can be introduced into different body cavities, such as via a femoral vein, a jugular vein, an axillary vein, or a subclavian vein. Alternatively, catheter 100 can be introduced directly into the chambers of the heart via introduction at the apex of the left ventricle.

At step 502, guide wire tip 109 is advanced to and through the LAA ostium, and into the LAA cavity. For example, if guide wire tip 109 was introduced into the body cavity via the femoral vein, then guide wire tip 109 can be advanced transseptally to and through the LAA ostium, and into the LAA cavity using an endovascular approach.

Figure 6:
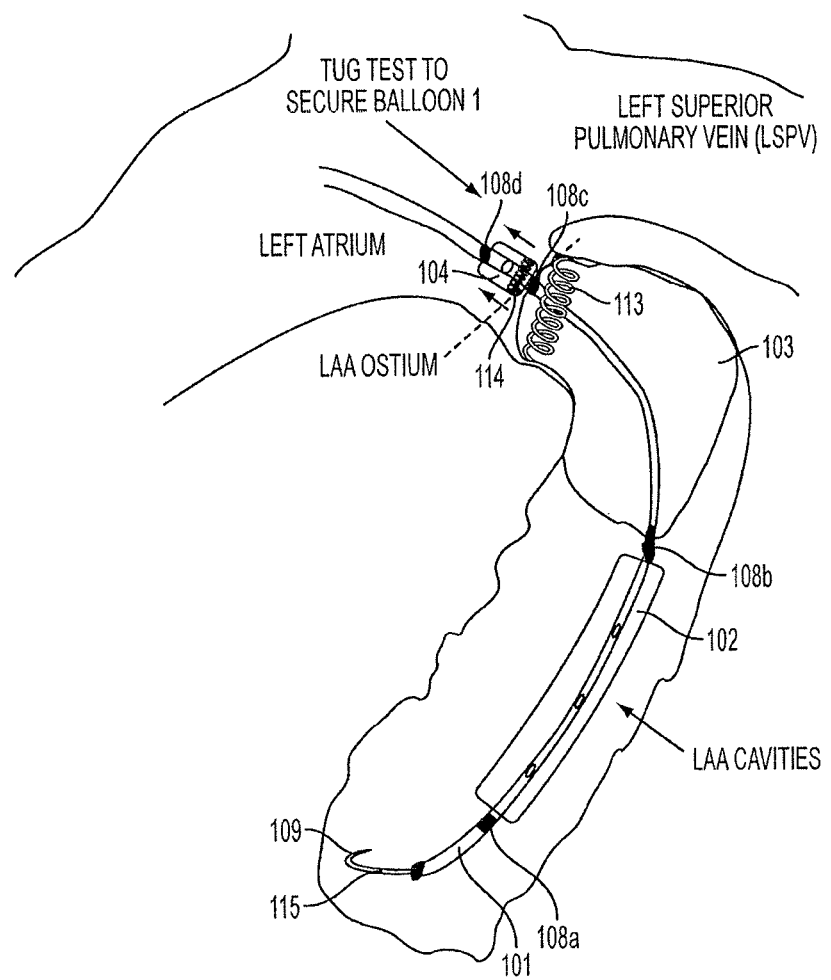
FIG. 6 is a first perspective view of the exemplary embodiment of FIG. 1 when deployed into the LAA.
Figure 7:
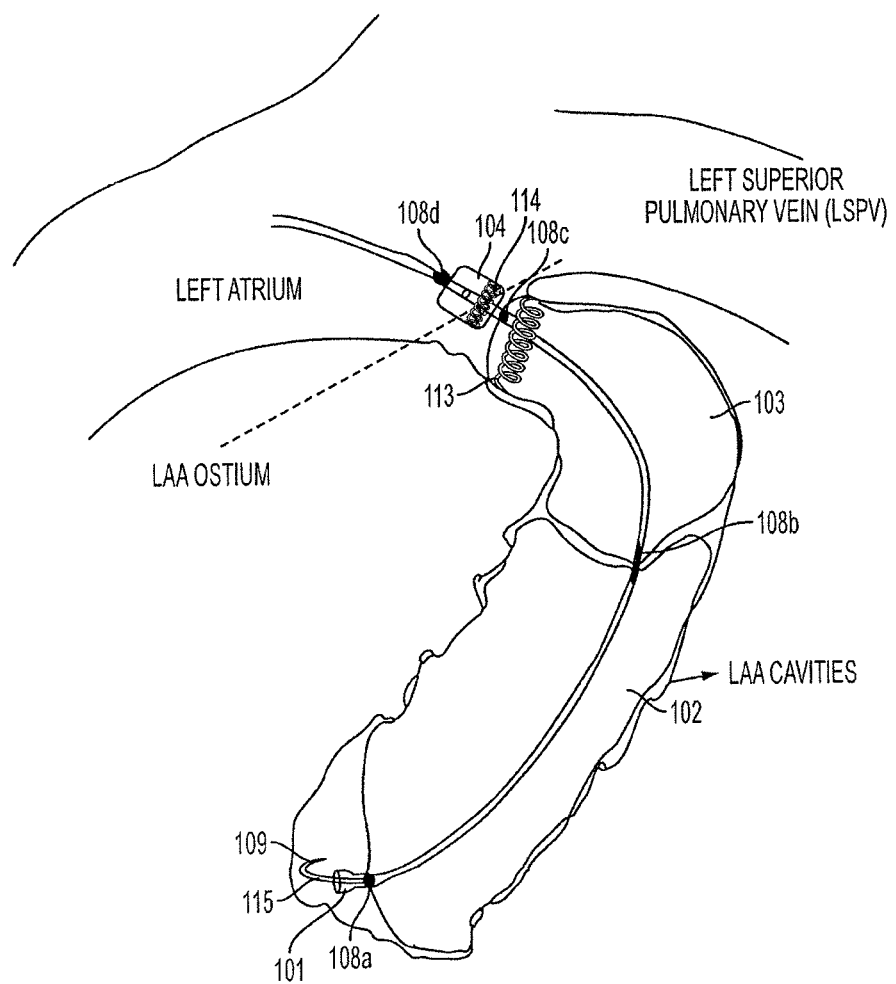
FIG. 7 is a second perspective view of the exemplary embodiment of FIG. 1 when deployed into the LAA.

At step 503, catheter sheath 101 is advanced towards the direction of guide wire tip 109. For example, if guide wire tip 109 was introduced into the body cavity via the femoral vein, then catheter sheath 101 can be advanced transseptally to and through the LAA ostium, and into the LAA cavity using an endovascular approach. As shown in FIGS. 6-8, catheter sheath 101 is advanced until it is close to, but prior to, guide wire tip 109. By way of example, as shown in FIGS. 6-8, catheter sheath 101 is advanced until inflatable catheter balloon 103 advances through the LAA ostium and slightly into the LAA cavity. Radiopaque marker band 108c can provide guidance as to when inflatable catheter balloon 103 advances through the LAA ostium and slightly into the LAA cavity.

At step 504, inflatable catheter balloon 103 having electromagnetic coils 113 is inflated distal to the LAA ostium, as shown in FIG. 6. Inflatable catheter balloon 103 is inflated by the input of air, or a liquid that is mixed with radiopaque contrast, via inflation port 111 through catheter sheath openings 106a, 106b, and 106c. When inflated, the shape of inflatable catheter balloon 103 assumes the contours of its surroundings in the LAA cavity. By assuming the contours of its surroundings, inflatable catheter balloon 103 occludes the LAA ostium as well as the potential sites for tear or perforation in the LAA cavity, thereby treating and preventing bleeding arising from the LAA. Also, when inflatable catheter balloon 103 is inflated, electromagnetic coils 113 located within the proximal portions of inflatable catheter balloon 103 also expand. Thus, when expanded, electromagnetic coils 113 are located immediately distal to the LAA ostium, as shown in FIG. 6.

At step 505, a tug test is performed to ensure that inflatable catheter balloon 103 firmly occludes the LAA ostium, as shown in FIG. 6. A "tug test" is a term of art known to one skilled in the art. In this embodiment, the tug test is the pulling back of inflatable catheter balloon 103, from the LAA cavity and towards the LAA ostium, in a manner that firmly occludes the LAA ostium.

At step 506, inflatable catheter balloon 102 is inflated distal to inflatable catheter balloon 103, as shown in FIG. 7. Inflatable catheter balloon 102 is inflated by the input of air, or a liquid that is mixed with radiopaque contrast, via inflation port 111 through catheter sheath openings 105a, 105b, and 105c. When inflated, the shape of inflatable catheter balloon 102 assumes the contours of its surroundings in the LAA cavity, as shown in FIG. 7. By assuming the contours of its surroundings, inflatable catheter balloon 102 occludes the potential sites for tear or perforation in the LAA cavity, thereby treating and preventing bleeding arising from the LAA.

At step 507, inflatable catheter balloon 104 having electromagnetic coils 114 is inflated proximal to the LAA ostium, as shown in FIG. 8. Inflatable catheter balloon 104 is inflated by the input of air, or a liquid that is mixed with radiopaque contrast, via inflation port 111 through catheter sheath opening 107. When inflatable catheter balloon 104 is inflated, electromagnetic coils 114 located within the distal portions of inflatable catheter balloon 104 also expand. Thus, when expanded, electromagnetic coils 114 are located immediately proximal to the LAA ostium, as shown in FIG. 8. Thus, by way of electromagnetic forces via the interaction of electromagnetic coils 113 and 114, inflatable catheter balloons 103 and 104 are attracted towards and adhere to each other, thereby causing these balloons to firmly occlude the LAA ostium, as shown in FIG. 8. When inflated, inflatable catheter balloon 104 has a diameter larger than that of the LAA ostium, and larger than that of inflatable catheter balloon 103. Thus, when inflated, inflatable catheter balloon 104 has a circumference larger than that of the LAA ostium, and larger than that of inflatable catheter balloon 103. This ensures that the LAA ostium is firmly occluded, as shown in FIG. 8. By firmly occluding the LAA ostium, any bleeding arising from the LAA is treated and prevented.

Finally, at step 508, the LAA cavity is punctured in a direction from within the LAA cavity and into the pericardial cavity so that there is no risk of bleeding into the pericardial space. In particular, a tip of the LAA cavity can be punctured using catheter sheath 101.

FIGS. 6-8 are perspective views of the exemplary embodiment of FIG. 1 when deployed into the LAA.

Figure 9:
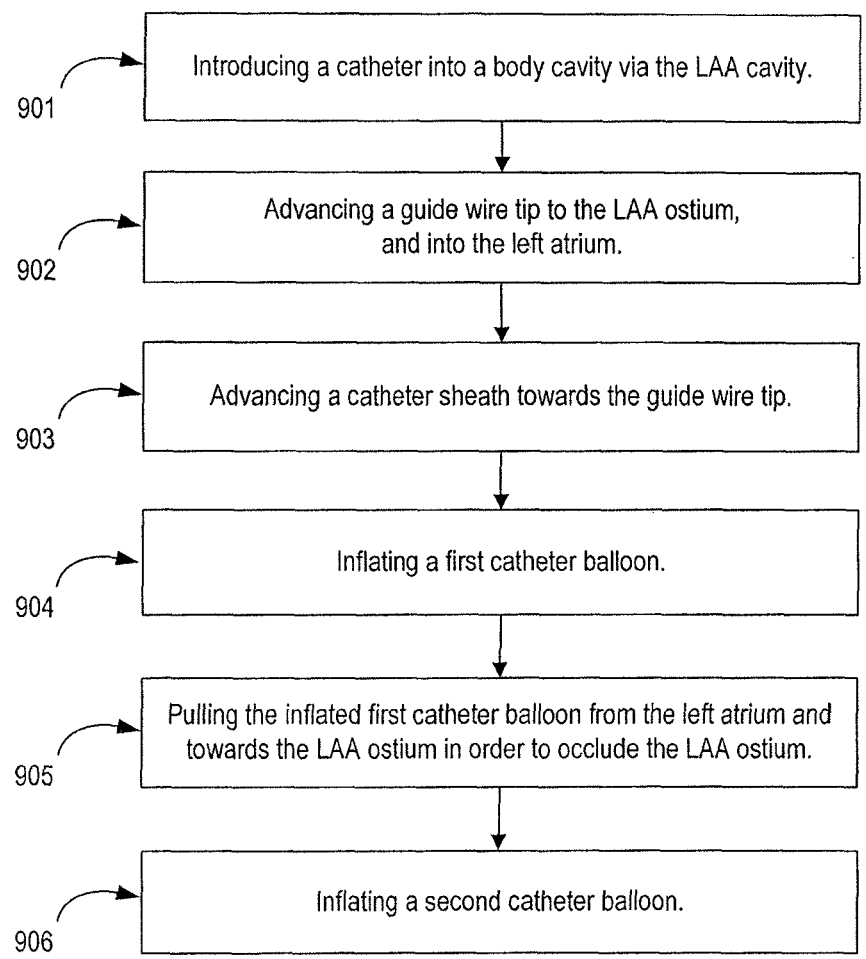
FIG. 9 is a flowchart depicting an exemplary embodiment of the present invention's method for treating and preventing bleeding arising from the LAA utilizing catheter 200 as shown in FIGS. 3, and 10-12.
Figure 10:
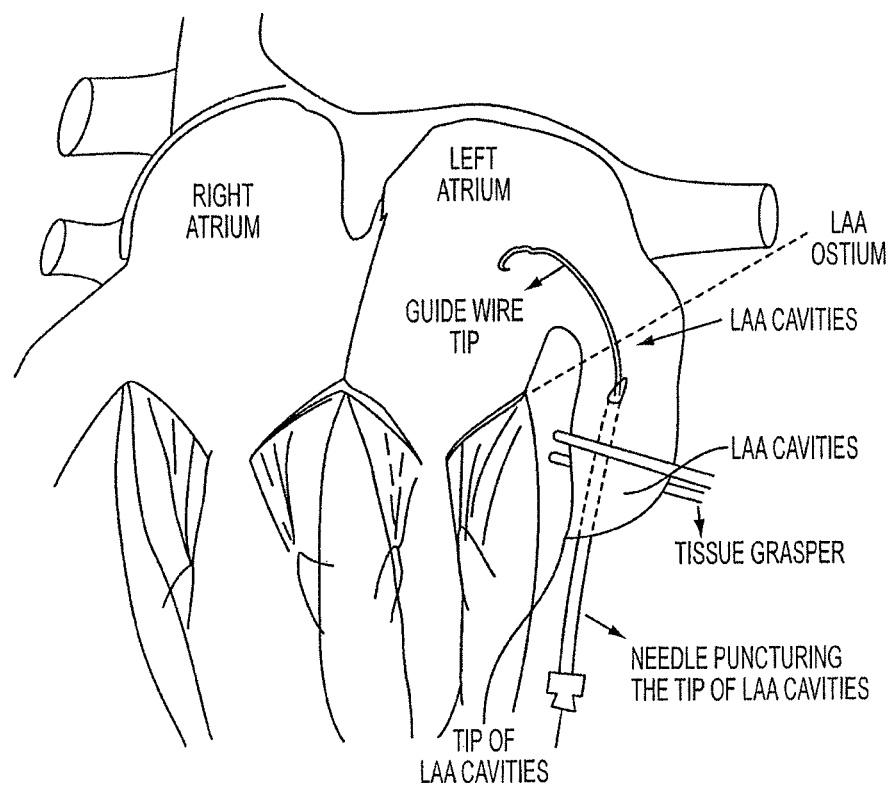
FIG. 10 is a first perspective view of the exemplary embodiment of FIG. 3 when deployed into the LAA.

FIG. 9 is a flowchart depicting an exemplary embodiment of the present invention's method for treating and preventing bleeding arising from the LAA utilizing catheter 300 as shown in FIGS. 3, and 10-12. At step 901, catheter 300 is introduced into a body cavity via the LAA cavity. For example, guide wire tip 307 is introduced into the body cavity via a puncture and an insertion at the tip of the LAA cavity, as shown in FIG. 10. As shown in FIG. 10, a tissue grasper with soft jaws of varying width is used to hold the LAA stationary while the tip of the LAA cavity is punctured with, for example, a hollow needle. This tissue grasper also serves to maintain hemostasis. Next, the guide wire tip 307 is introduced into the body cavity via a punctured location at the tip of the LAA, and into the LAA cavity.

At step 902, guide wire tip 307 is advanced to and through the LAA ostium, and into the left atrium, as shown in FIG. 10.

At step 903, catheter sheath 301 is advanced towards the direction of guide wire tip 307, as shown in FIG. 11. Accordingly, as shown in FIG. 11, catheter sheath 301 is advanced to and through the LAA ostium, and into the left atrium. As shown in FIG. 11, catheter sheath 301 is advanced until it is close to, but prior to, guide wire tip 307.

At step 904, inflatable catheter balloon 302 having electromagnetic coils 311 is inflated at the tip of catheter sheath 301, as shown in FIG. 11. Inflatable catheter balloon 302 is inflated by the input of air, or a liquid that is mixed with radiopaque contrast, via inflation port 309 through catheter sheath openings 304a, 304b, and 304c. When inflatable catheter balloon 302 is inflated, electromagnetic coils 311 located within the proximal portions also expand, as shown in FIG. 11.

At step 905, the inflated catheter balloon 302 is pulled back, from the left atrium towards the LAA ostium, to occlude the LAA ostium, as shown in FIG. 11.

Finally, at step 906, inflatable catheter balloon 303 having electromagnetic coils 312 is inflated near the LAA ostium, as shown in FIG. 12. Inflatable catheter balloon 303 is inflated by the input of air, or a liquid that is mixed with radiopaque contrast, via inflation port 309 through catheter sheath openings 305a, 305b, and 305c. When inflated, the shape of inflatable catheter balloon 303 assumes the contours of its surroundings in the LAA cavity, as shown in FIG. 12. By assuming the contours of its surroundings, inflatable catheter balloon 303 occludes the potential sites for tear or perforation in the LAA cavity, thereby treating and preventing bleeding arising from the LAA. When inflatable catheter balloon 303 is inflated, electromagnetic coils 312 located within the distal portions of inflatable catheter balloon 303 also expand, as shown in FIG. 12. By way of electromagnetic forces via the interaction of electromagnetic coils 311 and 312, inflatable catheter balloons 302 and 303 are attracted towards and adhere to each other, thereby causing these balloons to firmly occlude the LAA ostium, as shown in FIG. 12. By firming occluding the LAA ostium, any bleeding arising from the LAA is treated and prevented.

FIGS. 10-12 are perspective views of the exemplary embodiment of FIG. 3 when deployed into the LAA.

Figure 13:
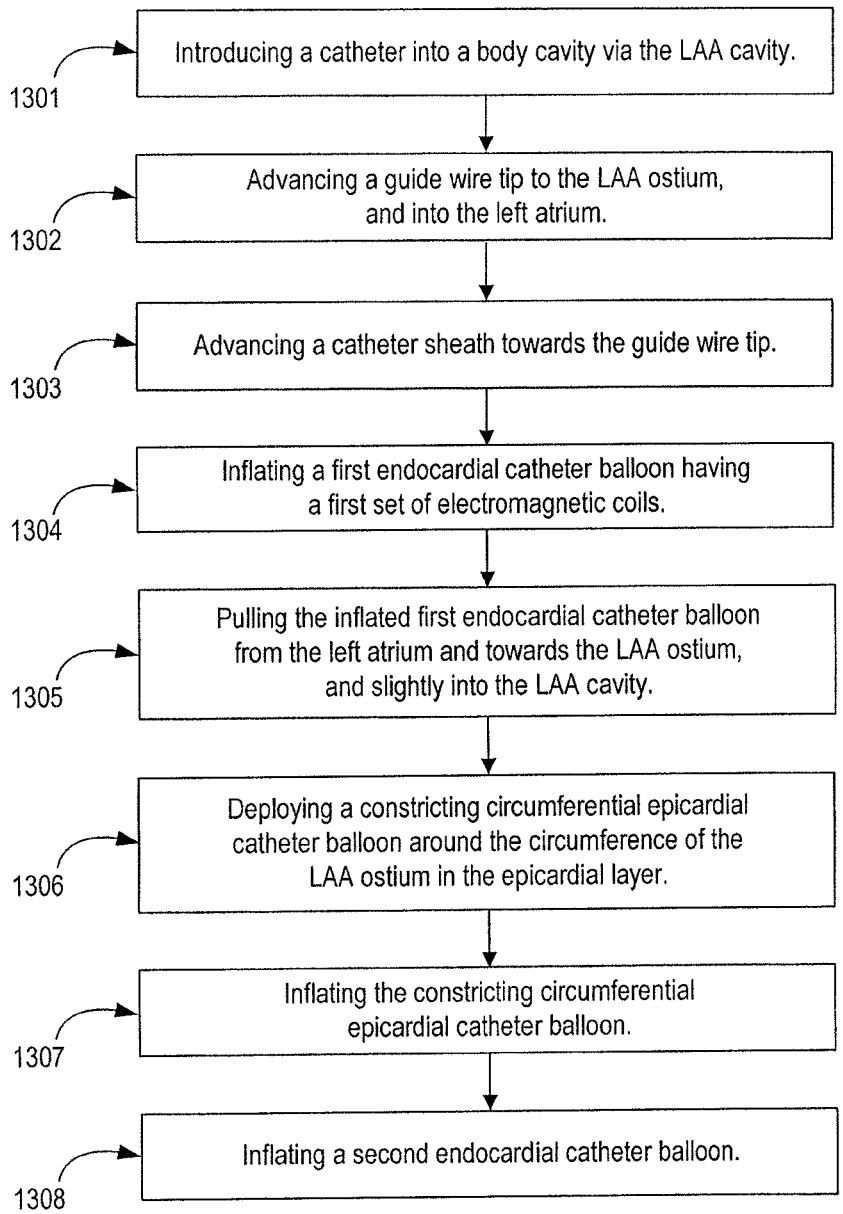
FIG. 13 is a flowchart depicting an exemplary embodiment of the present invention's method for treating and preventing bleeding arising from the LAA utilizing catheters 400 and 1800 as shown in FIGS. 4, 10, 14, and 18A-18B.

FIG. 13 is a flowchart depicting an exemplary embodiment of the present invention's method for treating and preventing bleeding arising from the LAA utilizing catheters 400 and 1800 as shown in FIGS. 4, 10, 14, and 18A-18B. At step 1301, catheter 400 is introduced into a body cavity via the LAA cavity. For example, guide wire tip 406 can be introduced into the body cavity via a puncture and an insertion at the tip of the LAA cavity, as shown in FIG. 10. As shown in FIG. 10, a tissue grasper with soft jaws of varying width is used to hold the LAA stationary while the tip of the LAA cavity is punctured with, for example, a hollow needle. This tissue grasper also serves to maintain hemostasis. Next, guide wire tip 406 is introduced into the body cavity via a punctured location at the tip of the LAA, and into the LAA cavity.

At step 1302, guide wire tip 406 is advanced to and through the LAA ostium, and into the left atrium, as previously shown in FIG. 10.

At step 1303, catheter sheath 401 is advanced towards the direction of guide wire tip 406. Accordingly, catheter sheath 401 is advanced to and through the LAA ostium, and into the left atrium. Catheter sheath 401 is advanced until it is close to, but prior to, guide wire tip 406.

At step 1304, inflatable endocardial catheter balloon 402 having electromagnetic coils 411 is inflated at the tip of catheter sheath 401. Inflatable endocardial catheter balloon 402 is inflated by the input of air, or a liquid that is mixed with radiopaque contrast, via inflation port 409 through catheter sheath openings 404a, 404b, and 404c. When inflatable endocardial catheter balloon 411 is inflated, electromagnetic coils 411 located within the distal portions of inflatable endocardial catheter balloon 402 also expand, as shown in FIG. 14.

At step 1305, inflated endocardial catheter balloon 402 is pulled back from the left atrium towards the LAA ostium, and slightly into the LAA cavity, as shown in FIG. 14. As shown in FIG. 14, when pulled back, electromagnetic coils 411, located within the proximal portions of inflated endocardial catheter balloon 402, align near the mid-point of the LAA ostium. Also, as shown in FIG. 14, in inflated endocardial catheter balloon 402, the end facing the left atrium has a larger diameter than that of the end facing the LAA cavity. Thus, as shown in FIG. 14, in inflated endocardial catheter balloon 402, the end facing the left atrium has a larger circumference than that of the end facing the LAA cavity.

Figure 18A:
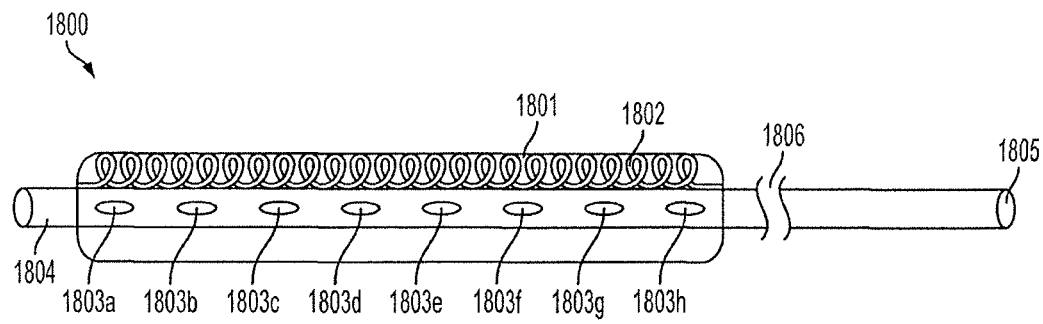
FIG. 18A is a perspective view of a fourth exemplary embodiment of the present invention's apparatus for treating and preventing bleeding arising from the LAA.
Figure 18B:
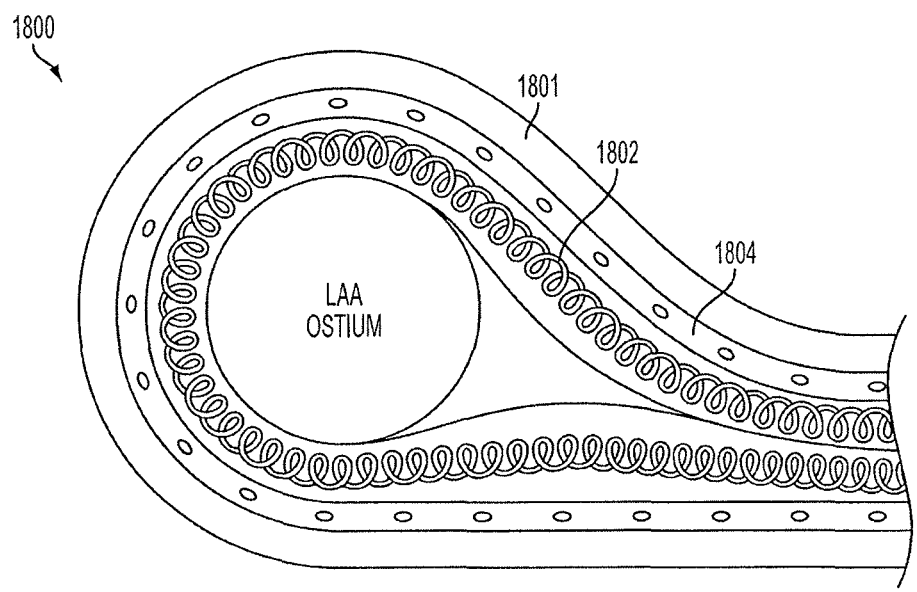
FIG. 18B is a perspective view of the exemplary embodiment of FIG. 18B when deployed around the LAA ostium.

At step 1306, constricting circumferential epicardial balloon 1801 having electromagnetic coils 1802 is deployed around the circumference of the LAA ostium in the epicardium layer of the heart, as shown in FIG. 18B. This deployment can be performed manually by a physician.

At step 1307, constricting circumferential inflatable epicardial catheter balloon 1801 is inflated. Inflatable epicardial catheter balloon 1801 is inflated by the input of air, or a liquid that is mixed with radiopaque contrast, via inflation port 1805 through catheter sheath openings 1803a-1803h. When inflated, electromagnetic coils 1802 located within constricting circumferential epicardial balloon 1802 also expand, as shown in FIGS. 14 and 18B. By way of electromagnetic forces via the interaction of electromagnetic coils 411 and 1802, inflatable endocardial catheter balloon 402 and inflatable epicardial catheter balloon 1802 are attracted towards each other, thereby forming a tight hemostatic seal, as shown in FIG. 14. This tight hemostatic seal helps treat and prevent bleeding arising from the LAA.

Finally, at step 1308, inflatable endocardial catheter balloon 403 is inflated in the LAA cavity, as shown in FIG. 14. Inflatable endocardial catheter balloon 403 is inflated by the input of air, or a liquid that is mixed with radiopaque contrast, via inflation port 409 through catheter sheath openings 405a, 405b, and 405c. When inflated, the shape of inflatable endocardial catheter balloon 403 assumes the contours of its surroundings in the LAA cavity, as shown in FIG. 14. By assuming the contours of its surroundings, inflatable endocardial catheter balloon 403 occludes the potential sites for tear or perforation in the LAA cavity, thereby treating and preventing bleeding arising from the LAA.

FIG. 14 is a perspective view of the exemplary embodiments of FIGS. 4 and 18A-18B when apparatus 400 is deployed into the LAA in the endocardial layer, and when apparatus 1800 is deployed around the LAA in the epicardial layer.

Figure 15:
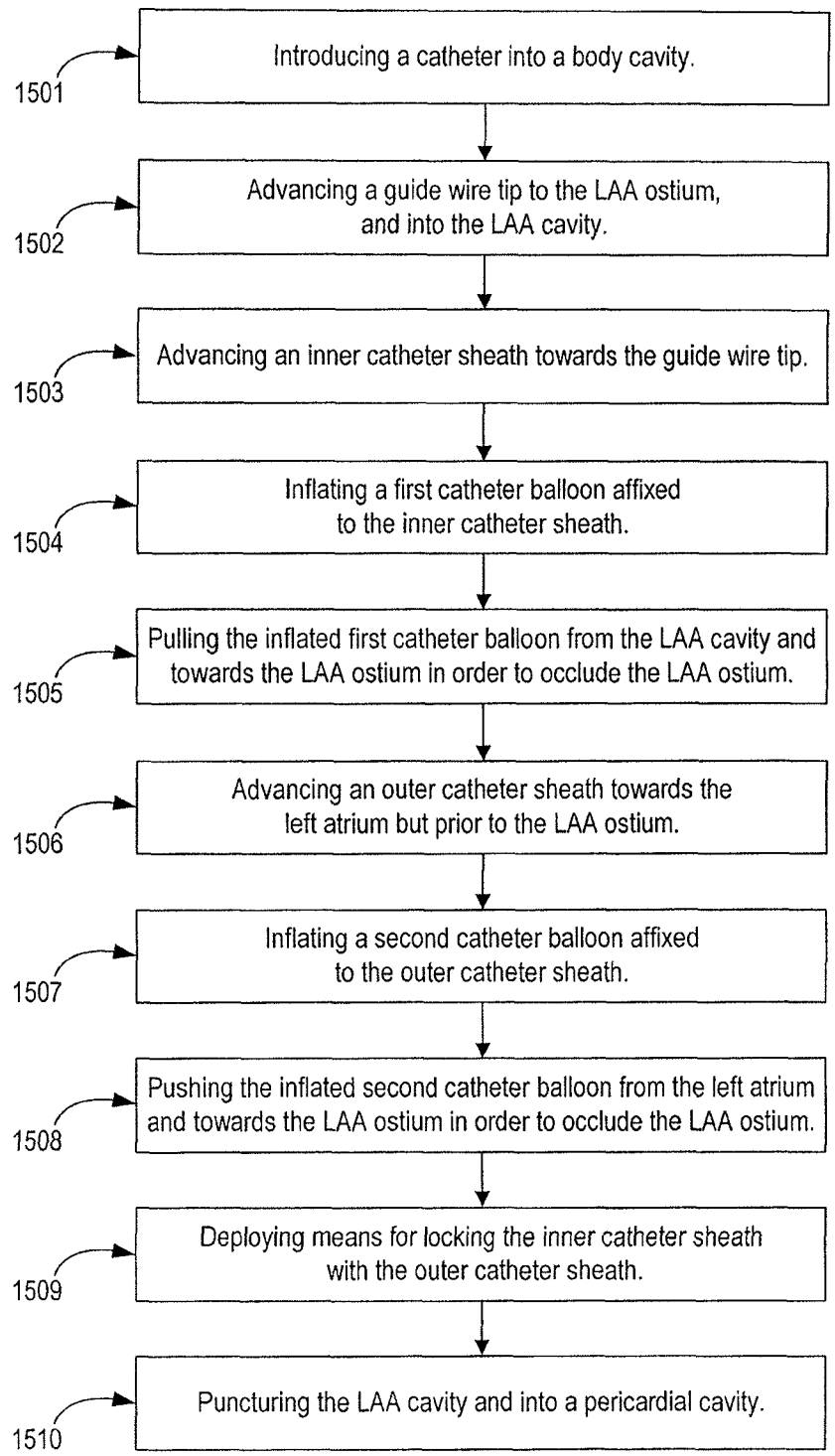
FIG. 15 is a flowchart depicting an exemplary embodiment of the present invention's method for treating and preventing bleeding arising from the LAA utilizing catheter 200 as shown in FIGS. 2, 16, and 17.

FIG. 15 is a flowchart depicting an exemplary embodiment of the present invention's method for treating and preventing bleeding arising from the LAA utilizing catheter 200 as shown in FIGS. 2, 16, and 17. At step 1501, catheter 100 is introduced into a body cavity. For example, catheter 200 can be introduced into a body cavity via a puncture and an insertion of guide wire tip 208 into the body. Catheter 200 can be introduced into different body cavities, such as via a femoral vein, a jugular vein, an axillary vein, or a subclavian vein. Alternatively, catheter 200 can be introduced directly into the chambers of the heart via introduction at the apex of the left ventricle.

At step 1502, guide wire tip 208 is advanced to and through the LAA ostium, and into the LAA cavity. For example, if guide wire tip 208 was introduced into the body cavity via the femoral vein, then guide wire tip 208 can be advanced transseptally to and through the LAA ostium, and into the LAA cavity using an endovascular approach.

At step 1503, inner catheter sheath 201 is advanced towards the direction of guide wire tip 208. As shown in FIG. 16, inner catheter sheath 201 is advanced until it is close to, but prior to, guide wire tip 208. For example, if guide wire tip 208 was introduced into the body cavity via the femoral vein, then inner catheter sheath 201 can be advanced until it is close to, but prior to, guide wire tip 208.

At step 1504, inflatable catheter balloon 202 is inflated distal to the LAA ostium, as shown in FIG. 16. Inflatable catheter balloon 202 is inflated by the input of air, or a liquid that is mixed with radiopaque contrast, via inflation port 212 through catheter sheath openings 205a, 205b, 205c.

At step 1505, inflated catheter balloon 202 is pulled, from the LAA cavity and towards the LAA ostium, to occlude the LAA ostium. Also, the shape of inflated catheter balloon 202 assumes the contours of its surroundings in the LAA cavity. By assuming the contours of its surroundings, inflatable catheter balloon 202 occludes the potential sites for tear or perforation in the LAA cavity, thereby treating and preventing bleeding arising from the LAA.

At step 1506, outer catheter sheath 203 is advanced towards the direction of guide wire tip 208. However, as shown in FIG. 16, outer catheter sheath 203 is advanced until it reaches the left atrium and prior to the LA ostium. For example, if guide wire tip 208 was introduced into the body cavity via the femoral vein, then out catheter sheath 203 can be advanced until it reaches the left atrium and prior to the LA ostium.

At step 1507, inflatable catheter balloon 204 is inflated while it is in the left atrium. Inflatable catheter balloon 204 is inflated by the input of air, or a liquid that is mixed with radiopaque contrast, via inflation port 212 through catheter sheath openings 206a and 206b.

At step 1508, inflated catheter balloon 204 is from the left atrium and towards the LAA ostium. When inflated, inflatable catheter balloon 204 has a diameter larger than that of the LAA ostium, and larger than that of inflatable catheter balloon 202, as shown in FIG. 16. Thus, when inflated, catheter balloon 204 has a circumference larger than that of the LAA ostium, and larger than that of inflatable catheter balloon 202. This ensures that the LAA ostium is firmly occluded, as shown in FIG. 16. By firming occluding the LAA ostium, any bleeding arising from the LAA is treated and prevented.

At step 1509, locking means 209 is deployed to render inflated catheter balloons 202 and 204 stationary. Locking means 209 is a spring-loaded device housed in inner catheter sheath 202 that upon deployment, it would bulge out through the corresponding slots in outer catheter sheath 203, thereby locking in place inflated catheter balloons 202 and 204.

Finally, at step 1510, the LAA cavity is punctured in a direction from within the LAA cavity and into the pericardial cavity so that there is no risk of bleeding into the pericardial space. In particular, a tip of the LAA cavity can be punctured using inner catheter sheath 202.

FIG. 16 is a perspective view of the exemplary embodiment of FIG. 2 when deployed into the LAA. FIG. 17 is a perspective view of the locking means in the exemplary embodiment of FIG. 2.

FIG. 18A is a perspective view of a fourth exemplary embodiment of the present invention's apparatus for treating and preventing bleeding arising from the LAA. FIG. 18B is a perspective view of the exemplary embodiment of FIG. 18B when deployed around the LAA ostium. FIG. 18A shows a stand-alone catheter 1800 before it is introduced into a body cavity. Hence, FIG. 18A shows constricting circumferential epicardial balloon 1801 in its un-inflated form. Constricting circumferential epicardial balloon 1801 is affixed to catheter sheath 1804. As previously articulated, depending on the desired degree of compliance, constricting circumferential epicardial balloon 1801 can be made of rubber, latex, polyisoprene, silicone, polyurethane, or any combination thereof. It is contemplated that constricting circumferential epicardial balloon 1801 can be compliant, semi-compliant, or non-compliant. Additionally, it is contemplated that catheter 1800 can be made up of more than one constricting circumferential epicardial balloon.

Constricting circumferential epicardial balloon 1801 is inflated by the input of air, or a liquid that is mixed with radiopaque contrast, via inflation port 1805 through catheter sheath openings 1803a-1803h. It is contemplated that the number of catheter sheath openings can vary. For example, constricting circumferential epicardial balloon 1801 can be inflated via inflation port 1805 through only one catheter sheath opening, or through more than eight catheter sheath openings. Inflation port 1805 provides the portal for the input of air, or a liquid that is mixed with radiopaque contrast, by, for example, a balloon catheter inflation device.

Electromagnetic coils 1802 are located within constricting circumferential epicardial balloon 1801. When constricting circumferential epicardial balloon 1801 is inflated, electromagnetic coils 1802 also expand, as shown in FIGS. 14 and 18B. Electromagnetic coils 1802 are insulated wires coiled together to form a solenoid, and thus, can be made out of copper or any other metallic wire capable of conducting electricity.

As duly noted by elongation identifier 1806, the length of catheter sheath 1804 can vary depending on the circumference of the particular patient's LAA ostium. Similarly, the length of constricting circumferential epicardial balloon 1801 can also vary depending on the circumference of the particular patient's LAA ostium.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

Additional Disclosures

The following disclosures provide a summary of the invention's various apparatuses used with the appended claims. In an exemplary embodiment, a catheter for treating and preventing bleeding arising from a LAA comprises a guide wire with a guide wire tip, a catheter sheath, a first inflatable catheter balloon affixed to the catheter sheath, wherein the first catheter balloon is proximal to the guide wire tip, a second inflatable catheter balloon affixed to the catheter sheath, wherein the second catheter balloon is proximal to the first catheter balloon, a first set of electromagnetic coils located within the second catheter balloon, a third inflatable catheter balloon affixed to the catheter sheath, wherein the third catheter balloon is proximal to the second catheter balloon, a second set of electromagnetic coils located within the third catheter balloon, a plurality of catheter sheath openings on the catheter sheath, wherein each catheter sheath opening is enclosed by one of the catheter balloons, and wherein each of the catheter balloons encloses at least one catheter sheath opening, an inflation port, and a control port. The catheter further comprises at least one radiopaque marker band affixed to the catheter sheath. The catheter wherein the first catheter balloon is more compliant than the second catheter balloon. The catheter wherein the second catheter balloon is more compliant the third catheter balloon. The catheter wherein the third catheter balloon, when inflated, has a larger circumference than that of an ostium of the LAA. The catheter wherein the third catheter balloon, when inflated, has a larger circumference than that of the second catheter balloon. The catheter wherein the second catheter balloon, when inflated, has a larger circumference than that of the first catheter balloon. The catheter wherein the first set of electromagnetic coils is located within a proximal end of the second catheter balloon. The catheter wherein the second set of electromagnetic coils is located within a distal end of the third catheter balloon. The catheter wherein the guide wire tip is J-hooked. Furthermore, the catheter sheath can be used for puncturing the LAA cavity.

In another exemplary embodiment, a catheter for treating and preventing bleeding arising from a LAA comprises a guide wire with a guide wire tip, an inner catheter sheath, an outer catheter sheath, a first inflatable catheter balloon affixed to the inner catheter sheath, wherein the first catheter balloon is proximal to the guide wire tip, at least one catheter sheath opening on the inner catheter sheath, wherein each catheter sheath opening is enclosed by the first catheter balloon, a second inflatable catheter balloon affixed to the outer catheter sheath, wherein the second catheter balloon is proximal to the first catheter balloon, at least one catheter sheath opening on the distal end of the outer catheter sheath, wherein each catheter sheath opening is enclosed by the second catheter balloon, an inflation port, and a control port. The catheter further comprises means for locking in place the inflated first and second catheter balloons. The catheter further comprises at least one radiopaque marker band affixed to the inner catheter sheath. The catheter further comprises at least one radiopaque marker band affixed to the outer catheter sheath. The catheter wherein the first catheter balloon is more compliant than the second catheter balloon. The catheter wherein the second catheter balloon, when inflated, has a larger circumference than that of an ostium of the LAA. The catheter wherein the second catheter balloon, when inflated, has a larger circumference than that of the first catheter balloon. The catheter wherein the guide wire tip is J-hooked. Furthermore, the inner catheter sheath has an additional lumen that can be used for puncturing the LAA cavity.

In another exemplary embodiment, a catheter for treating and preventing bleeding arising from a LAA comprises a guide wire with a guide wire tip, a catheter sheath, a first inflatable catheter balloon affixed to the catheter sheath, wherein the first catheter balloon is proximal to the guide wire tip, a first set of electromagnetic coils located within the first catheter balloon, a second inflatable catheter balloon affixed to the catheter sheath, wherein the second catheter balloon is proximal to the first catheter balloon, a plurality of catheter sheath openings on the catheter sheath, wherein each catheter sheath opening is enclosed by one of the catheter balloons, and wherein each of the catheter balloons encloses at least one catheter sheath opening, an inflation port, and a control port. The catheter further comprises at least one radiopaque marker band affixed to the catheter sheath. The catheter wherein the second catheter balloon is more compliant than the first catheter balloon. The catheter wherein the first catheter balloon, when inflated, has a larger circumference than that of an ostium of the LAA. The catheter wherein the first catheter balloon, when inflated, has a larger circumference than that of the second catheter balloon. The catheter wherein the first set of electromagnetic coils is located within a proximal end of the first catheter balloon. The catheter wherein the guide wire tip is J-hooked. The catheter wherein the distal portions of the first catheter balloon have a larger diameter than that of the proximal portions of the first catheter balloon. The catheter wherein the second catheter balloon further comprises a second set of electromagnetic coils. The catheter wherein the second set of electromagnetic coils is located within a distal end of the second catheter balloon. Furthermore, the catheter sheath can be used for puncturing the LAA cavity.

In another exemplary embodiment, a catheter for treating and preventing bleeding arising from a LAA comprises a guide wire with a guide wire tip, a catheter sheath, a first inflatable endocardial catheter balloon affixed to the catheter sheath, wherein the first endocardial catheter balloon is proximal to the guide wire tip, a first set of electromagnetic coils located within the first catheter balloon, a second inflatable endocardial catheter balloon affixed to the catheter sheath, wherein the second endocardial catheter balloon is proximal to the first endocardial catheter balloon, a plurality of catheter sheath openings on the catheter sheath, wherein each catheter sheath opening is enclosed by one of the endocardial catheter balloons, and wherein each of the endocardial catheter balloons encloses at least one catheter sheath opening, an inflation port, and a control port. The catheter further comprises at least one radiopaque marker band affixed to the catheter sheath. The catheter wherein the second endocardial catheter balloon is more compliant than the first endocardial catheter balloon. The catheter wherein the first endocardial catheter balloon, when inflated, has a larger circumference than that of an ostium of the LAA. The catheter wherein the first endocardial catheter balloon, when inflated, has a larger circumference than that of the second endocardial catheter balloon. The catheter wherein the first set of electromagnetic coils is located within a proximal end of the first endocardial catheter balloon. The catheter wherein the guide wire tip is J-hooked. The catheter wherein the distal portions of the first endocardial catheter balloon have a larger diameter than that of the proximal portions of the first endocardial catheter balloon. Furthermore, the catheter sheath can be used for puncturing the LAA cavity.

In another exemplary embodiment, a catheter for treating and preventing bleeding arising from a LAA comprises a catheter sheath, an inflatable constricting circumferential epicardial catheter balloon affixed to the catheter sheath, a set of electromagnetic coils located within the epicardial catheter balloon, a plurality of catheter sheath openings on the catheter sheath, wherein each catheter sheath opening is enclosed by the epicardial catheter balloon, and an inflation port. The catheter further comprises a control port. The catheter further comprises at least one radiopaque marker bands affixed to the catheter sheath. The catheter further comprises a guide wire with a guide wire tip. The catheter wherein the set of electromagnetic coils is located across the length of the epicardial catheter balloon. The catheter wherein the guide wire tip is J-hooked.

Finally, it is contemplated that the present invention can be used as an alternative approach to replace percutaneous aortic valves. Additionally, it is contemplated that the present invention can be used to perform a percutaneous repair of a mitral valve such as by an application of a clip to the mitral valve.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted.

What is claimed is:

1. A method for treating and preventing bleeding arising from a left atrial appendage (LAA), comprising the steps of:
   introducing a catheter into a body cavity;
   advancing a guide wire tip of the catheter to and past an ostium of the LAA, and into a cavity of the LAA;
   advancing an inner catheter sheath of the catheter towards the guide wire tip until the inner catheter sheath advances past the LAA ostium and into the LAA cavity;
   inflating, distal to the LAA ostium, a first inflatable catheter balloon, wherein the first catheter balloon is affixed to the inner catheter sheath;
   pulling the inflated first catheter balloon, from the LAA cavity and towards the LAA ostium, to occlude the LAA ostium;

advancing an outer catheter sheath of the catheter towards the guide wire tip until the outer catheter sheath advances past the LAA ostium and into a left atrium;

inflating, proximal to the LAA ostium, a second inflatable catheter balloon, wherein the second catheter balloon is affixed to the outer catheter sheath; and pushing the inflated second catheter balloon, from the left atrium and towards the LAA ostium, to occlude the LAA ostium.

2. The method of claim 1, further comprising the step of deploying means for locking in place the inflated first catheter balloon and the inflated second catheter balloon.

3. The method of claim 2, further comprising the step of:
puncturing the LAA cavity, wherein the puncturing is in a direction from within the LAA cavity and into a pericardial cavity.

4. The method of claim 1, wherein the body cavity is a femoral vein.

5. The method of claim 1, wherein the body cavity is a jugular vein.

6. The method of claim 1, wherein the body cavity is an axillary vein.

7. The method of claim 1, wherein the body cavity is a subclavian vein.

8. The method of claim 1, wherein the body cavity is an apex of a left ventricle.

9. A method for treating and preventing bleeding arising from a left atrial appendage (LAA), comprising the steps of:
introducing a catheter into a cavity of the LAA;
advancing a guide wire tip of the catheter to and past an ostium of the LAA, and into a left atrium;
advancing a catheter sheath of the catheter towards the guide wire tip until the catheter sheath advances past the LAA ostium and into the left atrium;
inflating, distal to the LAA ostium, a first inflatable catheter balloon having a first set of electromagnetic coils, wherein the first catheter balloon is affixed to the catheter sheath, and wherein upon inflation of the first catheter balloon, the first set of electromagnetic coils also expand;
pulling the inflated first catheter balloon, from the left atrium and towards the LAA ostium, to occlude the LAA ostium; and
inflating, proximal to the LAA ostium, a second inflatable catheter balloon, wherein the second catheter balloon is affixed to the catheter sheath.

10. The method of claim 9, further comprising the steps of:
deploying a constricting circumferential inflatable catheter balloon, having a second set of electromagnetic coils, around a circumference of the LAA ostium epicardially, wherein the constricting circumferential catheter balloon is affixed to a catheter sheath of another catheter; and
inflating the constricting circumferential catheter balloon, wherein upon inflation of the constricting circumferential catheter balloon, the second set of electromagnetic coils also expand.

11. The method of claim 9, wherein the second catheter balloon further includes a second set of electromagnetic coils, wherein upon inflation of the second catheter balloon, the second set of electromagnetic coils also expand.

* * * * *